US012643909B2

(12) United States Patent
Zhang

(10) Patent No.: US 12,643,909 B2
(45) Date of Patent: Jun. 2, 2026

(54) BIVALENT LIGANDS TO UNDERSTAND DIMERIZATION OF THE MU OPIOID RECEPTOR AND THE CHEMOKINE RECEPTOR CCR5 IN NEUROLOGICAL DISORDERS

(71) Applicant: VIRGINIA COMMONWEALTH UNIVERSITY, Richmond, VA (US)

(72) Inventor: Yan Zhang, Glen Allen, VA (US)

(73) Assignee: Virginia Commonwealth University, Richmond, VA (US)

( * ) Notice: Subject to any disclaimer, the term of this patent is extended or adjusted under 35 U.S.C. 154(b) by 428 days.

(21) Appl. No.: 18/552,761

(22) PCT Filed: Mar. 30, 2022

(86) PCT No.: PCT/US2022/022501
§ 371 (c)(1),
(2) Date: Sep. 27, 2023

(87) PCT Pub. No.: WO2022/212471
PCT Pub. Date: Oct. 6, 2022

(65) Prior Publication Data
US 2024/0208984 A1      Jun. 27, 2024

Related U.S. Application Data

(60) Provisional application No. 63/168,700, filed on Mar. 31, 2021.

(51) Int. Cl.
| | |
|---|---|
| *A61K 47/55* | (2017.01) |
| *A61K 9/19* | (2006.01) |
| *A61K 31/485* | (2006.01) |
| *C07D 489/08* | (2006.01) |
| *G01N 33/68* | (2006.01) |

(52) U.S. Cl.
CPC .............. *C07D 489/08* (2013.01); *A61K 9/19* (2013.01); *A61K 31/485* (2013.01); *A61K 47/55* (2017.08); *G01N 33/6863* (2013.01)

(58) Field of Classification Search
CPC .... C07D 489/08; A61K 47/55; A61K 31/485; A61K 9/19
See application file for complete search history.

(56) References Cited

U.S. PATENT DOCUMENTS

| | | |
|---|---|---|
| 2007/0167434 A1 | 7/2007 | Kesteleyn |
| 2015/0157730 A1* | 6/2015 | Zhang .................... A61P 25/00 |
| | | 514/282 |

OTHER PUBLICATIONS

Huang et al: "Structure-Based Design and Development of Chemical Probes Targeting Putative MOR-CCR5 Heterodimers to Inhibit Opioid Exacerbated HIV-1 Infectivity", Journal of Medicinal Chemistry, vol. 64, p. 7702-7723, May 24, 2021.
Yuan et al: "Design and Synthesis of a Bivalent Ligand to Explore the Putative Heterodimerization of the Mu Opioid Receptor and the Chemokine Receptor CCR5", Org Biomol Chem., vol. 10, No. 13, Mar. 26, 2015.

* cited by examiner

*Primary Examiner* — Sarah Pihonak
*Assistant Examiner* — Mikhail O'Donnel Robinson
(74) *Attorney, Agent, or Firm* — WCF IP

(57)      ABSTRACT

Bivalent ligands which bind to MOR-CCR5 heterodimers are provided. The bivalent ligands comprise two discrete pharmacophores, naltrexone and maraviroc, linked by a spacer and bind to MOR-CCR5 heterodimers, e.g. at the surface of a cell. The bivalent ligands are useful in assays to detect MOR-CCR5 heterodimers, as therapeutic agents to prevent and/or treat diseases characterized by the presence of MOR-CCR5 heterodimers.

17 Claims, 9 Drawing Sheets

YZMC013 (n = 5)
YZMC017 (n = 7)
YZMC019 (n = 3)

BIVALENT LIGANDS TO UNDERSTAND DIMERIZATION OF THE MU OPIOID RECEPTOR AND THE CHEMOKINE RECEPTOR CCR5 IN NEUROLOGICAL DISORDERS

CROSS-REFERENCE TO RELATED APPLICATIONS

This application claims benefit of U.S. provisional application 63/168,700 filed Mar. 31, 2021

STATEMENT OF FEDERALLY SPONSORED RESEARCH AND DEVELOPMENT

This invention was made with government support under Grant R01 DA044855 and Grant R01 DA034231, both awarded by National Institutes of Health/National Institute on Drug Abuse. The United States government has certain rights in the invention.

BACKGROUND OF THE INVENTION

Technical Field

The invention generally relates to bivalent ligand. In particular, the invention provides bivalent ligands comprising naltrexone and maraviroc pharmacophores linked by a spacer, for assaying cells for the presence of MOR-CCR5 heterodimers dimers and for preventing and/or treating neurological diseases, such as neuro-AIDS.

Description of Related Art

The opioid epidemic in the United States is a significant public health crisis. A recent report suggested that opioids were involved in 69.5% of all drug overdose deaths in the United States during 2018. AIDS (acquired immune deficiency syndrome), caused by HIV infection, remains another major public health issue with approximately 37.9 million people infected globally in 2018 and an estimated 38,000 new cases reported in the United States each year. Currently, the opioid abuse epidemic is closely associated with AIDS/HIV infection. Opioid use disorder (OUD) increases the risk of transmission of HIV infection directly through sharing needles, syringes, or other drug injection materials. It was reported that injection drug abuse accounted for 7% of all new HIV diagnoses in 2018 in the United States. Conversely, HIV infection can elevate the susceptibility to drug addiction as well. It has been estimated that HIV-infected individuals prescribed opioids were 21% to 53% more likely to have OUD than uninfected individuals. Moreover, long-term opioid use increases the risk of death among the HIV-infected population compared to uninfected individuals. Therefore, it is important to uncover the relationship between opioid use and enhanced HIV infectivity with the goal of limiting the spread and pathophysiological consequences of HIV.

Chronic opioid exposure tends to severely suppress both innate and adaptive immune functions, resulting in significantly increased vulnerability to infectious pathogens, such as HIV. Opioids can increase HIV replication and exacerbate the progression of AIDS. One possible pathway for opioid-mediated increased HIV replication occurs through the opioid-dependent upregulation of the major chemokine co-receptor CCR5. As is well known, opioid addiction liability is predominantly mediated via actions at the mu opioid receptor (MOR). Mounting studies have shown that MOR agonists, such as DAMGO ([D-Ala2-MePhe4-Gly(ol)5]enkephalin), morphine, and methadone, can induce elevated CCR5 receptor expression in different immune and non-immune cells. An increase in CCR5 expression furnishes additional viral entry sites and thus promotes HIV-1 infection/replication.

Accumulating in vitro studies suggest there is functional crosstalk between the MOR and CCR5, both belonging to the G-protein-coupled receptor (GPCR) superfamily. Previous reports have suggested that MOR-CCR5 crosstalk is, in part, mediated by the formation of putative MOR-CCR5 heterodimers. For example, using a co-immunoprecipitation approach, Suzuki et al. demonstrated that the MOR and CCR5 could form oligomers at the cell membrane of human or monkey lymphocytes and the oligomerization can modulate the function of both receptors. In addition, Chen and co-workers investigated possible mechanisms of cross-desensitization between the MOR and CCR5 coexpressed in Chinese hamster ovary (CHO) cells. They proposed that MOR-CCR5 heterodimerization may contribute to the observed cross-desensitization. Thus, putative MOR-CCR5 heterodimerization affects immune cell function and appears to contribute to the synergistic effects of opioids and HIV co-exposure in neuro-HIV progression.

Bivalent ligands containing two discrete pharmacophores tethered by an appropriate spacer are powerful chemical probes to characterize GPCR dimerization. Bivalent ligands that are capable of interacting simultaneously with both receptors would help facilitate the study of the putative MOR-CCR5 heterodimer and its role in opioid accelerated HIV entry/replication and could be useful in the prevention and/or treatment of diseases and conditions related to (e.g. characterized by), associated with or caused by MOR-CCR5 heterodimerization, such as HIV infection in opioid users.

To understand how MOR-CCR5 dimerization uniquely alters the function of each receptor, a bivalent ligand, VZMC001 (FIG. 1C), containing the MOR antagonist pharmacophore naltrexone (1, FIG. 1A) and the CCR5 antagonist pharmacophore maraviroc (2, FIG. 1B) was previously designed and synthesized. Naltrexone, a selective MOR antagonist, has been used in the treatment of OUD and maraviroc is the only marketed anti-HIV drug that blocks the CCR5 coreceptor function.

When the project utilizing naltrexone and maraviroc as pharmacophores was initiated, the ligand-bound crystal structures of the MOR and CCR5 were not available for structure-based molecular design, yet it was critical to choose appropriate spacers as well as suitable spacer attachment points on each pharmacophore to establish a desirable bivalent ligand. The C6-position of naltrexone was selected as an attachment point that could be transformed to the 60-amino group and the 4'-position of the terminal phenyl ring in maraviroc was selected as the second attachment point. Furthermore, several studies had indicated that a spacer with 21 atoms might be ideal to yield the optimal pharmacological effects. Therefore, the bivalent ligand VZMC001 with a 21-atom spacer linked through the corresponding attachment points on both pharmacophores was designed and prepared (FIG. 1C). Two monovalent ligands VZMC002 (containing the MOR antagonist pharmacophore only, FIG. 1D) and VZMC003 (containing the CCR5 antagonist pharmacophore only, FIG. 1E) were also constructed as controls to examine the potential influence of the spacer on the pharmacological effects on each pharmacophore.

Unfortunately, VZMC001 possessed unfavorable binding affinity profiles for both the MOR and CCR5 compared to the corresponding monomeric ligands. Moreover, results from molecular dynamics simulation showed that the maraviroc portion of VZMC001 was partially dislodged from the CCR5 binding pocket. Thus, VZMC001 was not a viable candidate for assaying cells for the presence of MOR-CCR5 dimers, for decreasing the ability of opioids to increase susceptibility to HIV infection or for preventing and/or treating HIV infections.

The failure of VZMC001 to function as a useful bivalent ligand for these purposes necessitated the development of new and improved bivalent ligands comprising the MOR and CCR5 antagonists naltrexone and maraviroc.

SUMMARY OF THE INVENTION

Other features and advantages of the present invention will be set forth in the description of invention that follows, and in part will be apparent from the description or may be learned by practice of the invention. The invention will be realized and attained by the compositions and methods particularly pointed out in the written description and claims hereof.

Disclosed herein are bivalent ligands targeting MOR-CCR5 heterodimers. The bivalent ligands comprise two discrete pharmacophores, naltrexone and maraviroc, linked by a spacer. They are used for assaying cells for the presence of MOR-CCR5 heterodimers, for example, to investigate the role of MOR-CCR5 heterodimers in the susceptibility to, the development of, the progression of and/or the treatment of neurological diseases and conditions such as neuro-AIDS, neurodegradation, dementia, etc. In addition, the bivalent ligands are used to prevent and/or treat these diseases and conditions.

In one aspect, the bivalent ligand is the exemplary bivalent ligand VZMC013. VZMC013 has been shown to possess nanomolar level binding affinities for both the MOR and CCR5, to inhibit CCL5-stimulated calcium mobilization, and to exhibit remarkably improved anti-HIV-1BaL activity compared to previously reported bivalent ligands. VZMC013 inhibited viral infection in TZM-b1 cells co-expressing CCR5 and MOR to a greater degree than cells expressing CCR5 alone. Furthermore, VZMC013 blocked HIV-1 entry into PBMC cells in a concentration-dependent manner, and inhibited opioid-accelerated HIV-1 entry more effectively in PHA-stimulated PBMC cells than in the absence of opioids. A 3D molecular model of VZMC013 binding to the MOR-CCR5 heterodimer complex is disclosed to elucidate its mechanism of action. VZMC013 is an example of a potent chemical probe targeting MOR-CCR5 heterodimers and also serves as a pharmacological agent to inhibit opioid-exacerbated HIV-1 entry into cells.

It is an object of this disclosure to provide bivalent ligand having Formula I:

Formula I where L is where n ranges from 0 to 12, * indicates a point of attachment to naltrexone; and ** indicates a point of attachment to maraviroc;
or where n ranges from 0 to 12, * indicates a point of attachment to naltrexone; and ** indicates a point of attachment to maraviroc;

or where n ranges from 0 to 12, * indicates a point of attachment to naltrexone; and ** indicates a point of attachment to maraviroc;

or where n ranges from 0 to 12, * indicates a point of attachment to naltrexone; and ** indicates a point of attachment to maraviroc;

or where n ranges from 0 to 12, * indicates the point of attachment to naltrexone; and ** indicates the point of attachment to maraviroc. In some aspects, the bivalent ligand is where n is 3, 5 or 7. In further aspects, the bivalent ligand is wherein n is 5.

In further aspects, the disclosure provides a lyophilized preparation comprising at least one bivalent ligand having Formula I:

Formula I where L is where n ranges from 0 to 12, * indicates a point of
attachment to naltrexone; and ** indicates a point of
attachment to maraviroc;

or where n ranges from 0 to 12, * indicates a point of
attachment to naltrexone; and ** indicates a point of
attachment to maraviroc;

or where n ranges from 0 to 12, * indicates a point of
attachment to naltrexone; and ** indicates a point of
attachment to maraviroc;

or where n ranges from 0 to 12, * indicates a point of
attachment to naltrexone; and ** indicates a point of
attachment to maraviroc;

or where n ranges from 0 to 12, * indicates the point of
attachment to naltrexone; and ** indicates the point of
attachment to maraviroc. In some aspects, the bivalent
ligand is where n is 3, 5 or 7. In further aspects, the bivalent ligand
is wherein n is 5. In further aspects, the at least one bivalent
ligand is labeled with at least one detectable label.

The disclosure also provides a preparation comprising at
least one bivalent ligand having Formula T:

Formula I where L is

5 where n ranges from 0 to 12, * indicates a point of
attachment to naltrexone; and ** indicates a point of
attachment to maraviroc;
or

10 where n ranges from 0 to 12, * indicates a point of
attachment to naltrexone; and ** indicates a point of
attachment to maraviroc;
or

35 where n ranges from 0 to 12, * indicates a point of
attachment to naltrexone; and ** indicates a point of
attachment to maraviroc;
or where n ranges from 0 to 12, * indicates a point of
attachment to naltrexone; and ** indicates a point of
attachment to maraviroc;
or

50 where n ranges from 0 to 12, * indicates the point of
attachment to naltrexone; and ** indicates the point of
attachment to maraviroc. In some aspects, the bivalent
ligand is

65 where n is 3, 5 or 7. In further aspects, the bivalent ligand is wherein n is 5; and a liquid carrier. In further aspects, the at least one bivalent ligand is labeled with at least one detectable label.

Also provided is a method of detecting a MOR-CCR5 heterodimer, comprising contacting the MOR-CCR5 heterodimer with bivalent ligand having Formula I:

Formula I where L is where n ranges from 0 to 12, * indicates a point of attachment to naltrexone; and ** indicates a point of attachment to maraviroc;

or where n ranges from 0 to 12, * indicates a point of attachment to naltrexone; and ** indicates a point of attachment to maraviroc;

or where n ranges from 0 to 12, * indicates a point of attachment to naltrexone; and ** indicates a point of attachment to maraviroc;

or where n ranges from 0 to 12, * indicates a point of attachment to naltrexone; and ** indicates a point of attachment to maraviroc;

or where n ranges from 0 to 12, * indicates the point of attachment to naltrexone; and ** indicates the point of attachment to maraviroc. In some aspects, the bivalent ligand is where n is 3, 5 or 7. In further aspects, the bivalent ligand is wherein n is 5, under conditions that permit the bivalent ligand to bind to and form a complex with the MOR-CCR5 heterodimer, and detecting the complex. In some aspects, the bivalent ligand is labeled with at least one detectable label. In further aspects, the method is an in vitro method or an in vivo method. In yet additional aspects, the MOR-CCR5 heterodimer is present on a cell.

The disclosure also provides a method of preventing or treating, in a subject in need thereof, a disease or condition characterized by the formation of MOR-CCR5 heterodimers, comprising administering to the subject a therapeutically effective amount of at least one bivalent ligand having Formula I:

Formula I where L is where n ranges from 0 to 12, * indicates a point of
attachment to naltrexone; and ** indicates a point of
attachment to maraviroc;
or where n ranges from 0 to 12, * indicates a point of
attachment to naltrexone; and ** indicates a point of
attachment to maraviroc;
or where n ranges from 0 to 12, * indicates a point of
attachment to naltrexone; and ** indicates a point of
attachment to maraviroc;
or where n ranges from 0 to 12, * indicates a point of
attachment to naltrexone; and ** indicates a point of
attachment to maraviroc;
or where n ranges from 0 to 12, * indicates the point of
attachment to naltrexone; and ** indicates the point of
attachment to maraviroc. In some aspects, the bivalent
ligand is where n is 3, 5 or 7. In further aspects, the bivalent ligand
is wherein n is 5. In some aspect, the disease or condition is
a neurological disease or condition selected from the
group consisting of neuro-AIDS, dementia, neurodeg-
radation, multiple sclerosis, neuropathic pain, chronic
pain or brain cancer. In further aspects, the disease or
condition is HIV.

Formula I

Also encompassed is a method of preventing or decreas-
ing opioid-induced susceptibility to HIV infection in a
subject in need thereof, comprising administering to the
subject a therapeutically effective amount of at least one
bivalent ligand having Formula T:

where L is where n ranges from 0 to 12, * indicates a point of
  attachment to naltrexone; and ** indicates a point of
  attachment to maraviroc;
  or where n ranges from 0 to 12, * indicates a point of
  attachment to naltrexone; and ** indicates a point of
  attachment to maraviroc;
  or where n ranges from 0 to 12, * indicates a point of
  attachment to naltrexone; and ** indicates a point of
  attachment to maraviroc;
  or where n ranges from 0 to 12, * indicates a point of
  attachment to naltrexone; and ** indicates a point of
  attachment to maraviroc;
  or where n ranges from 0 to 12, * indicates the point of
  attachment to naltrexone; and ** indicates the point of
  attachment to maraviroc. In some aspects, the bivalent
  ligand is where n is 3, 5 or 7. In further aspects, the bivalent ligand is wherein n is 5. In some aspects, the therapeutically effective amount is sufficient to permit the at least one bivalent ligand to bind to MOR-CCR5 heterodimers on cells of the subject.

Formula I

Also provided is a method of preventing or decreasing opioid-accelerated HIV-1 entry into a cell, comprising contacting the cell with at least one bivalent ligand having Formula I:

where L is

5 where n ranges from 0 to 12, * indicates a point of
attachment to naltrexone; and ** indicates a point of
attachment to maraviroc;
or

10

20 where n ranges from 0 to 12, * indicates a point of
attachment to naltrexone; and ** indicates a point of
attachment to maraviroc;
or

35 where n ranges from 0 to 12, * indicates a point of
attachment to naltrexone; and ** indicates a point of
attachment to maraviroc;
or where n ranges from 0 to 12, * indicates a point of
attachment to naltrexone; and ** indicates a point of
attachment to maraviroc;
or

50 where n ranges from 0 to 12, * indicates the point of
attachment to naltrexone; and ** indicates the point of
attachment to maraviroc. In some aspects, the bivalent
ligand is

65 where n is 3, 5 or 7. In further aspects, the bivalent ligand is wherein n is 5, wherein the step of contacting is performed under conditions that permit the bivalent ligand to bind to and form a complex with MOR-CCR5 heterodimers on the cell, and wherein formation of the complex prevents or decreases opioid-accelerated HIV entry into the cell.

BRIEF DESCRIPTION OF THE DRAWINGS

FIG. 1A-E. Chemical structures of A, naltrexone and B, maraviroc; C, the previously reported bivalent ligand VZMC001; D, VZMC002; E, VZMC003.

DETAILED DESCRIPTION

Figure 2A:
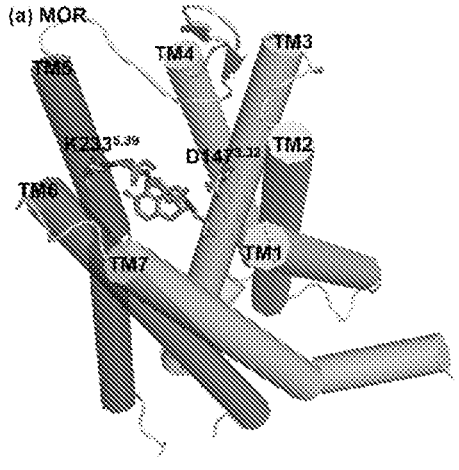
FIG. 2A-C. A, the binding mode of β-FNA in the MOR (adapted from PDB ID: 4DKL); B, the binding mode of maraviroc in the CCR5 (adapted from PDB ID: 4MBS); C, Structure-based molecular design of the second-generation bivalent ligands VZMC013, VZMC017, and VZMC019.
Figure 2B:
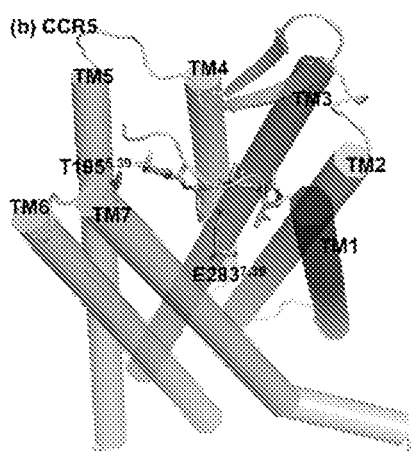

Provided herein are compounds (bivalent ligands) which are antagonists of the receptors MOR and CCR5, and of MOR-CCR5 heterodimers. The design, synthesis, and biological characterization this series of bivalent ligands is described as is their use to explore the biological and pharmacological process of the dimerization phenomenon between the mu opioid receptor (MOR) and the chemokine CCR5 receptor, e.g. in neurological disorders, and to treat such neurological disorders. The bivalent ligands contain two distinct pharmacophores linked through a spacer. Naltrexone and maraviroc were selected as the pharmacophores, since naltrexone interacts with the MOR and maraviroc interacts with the CCR5 receptor. Different types and lengths of linkers are disclosed.

The Compounds

The compounds have a general chemical formula as shown in Formula I:

where L is a linker (spacer) that connects the pharmacophores naltrexone and maraviroc between position 6 of naltrexone and position 3' of maraviroc, as shown. Features of linker L include but are not limited to aliphatic, aromatic, and/or peptidic chemical moieties in linear or ring forms connected through single, double or triple bond with a whole length from three Å to one hundred Å.

In some aspects, the linker is where n ranges from 0 to 12 (i.e. is 0, 1, 2, 3, 4, 5, 6, 7, 8, 9, 10, 11, or 12); * indicates the point of attachment to naltrexone; and ** indicates the point of attachment to maraviroc. The synthesis and characterization of bivalent ligands having this type of linker is discussed in the Examples. Generally, the overall reaction route to prepare these bivalent ligands was convergent and efficient, and involved sixteen steps with moderate to good yields.

Examples of such compounds include but are not limited to:

where n is 0 to 12 (i.e. is 0, 1, 2, 3, 4, 5, 6, 7, 8, 9, 10, 11, or 12), such as 3, 5, or 7. In yet further aspects, n is 5:

VZMC013

In other aspects, the linker is where n ranges from 0 to 12 (i.e. is 0, 1, 2, 3, 4, 5, 6, 7, 8, 9, 10, 11, or 12); * indicates the point of attachment to naltrexone; and ** indicates the point of attachment to maraviroc.

In other aspects, the linker is where n ranges from 0 to 12 (i.e. is 0, 1, 2, 3, 4, 5, 6, 7, 8, 9, 10, 11, or 12); * indicates the point of attachment to naltrexone; and ** indicates the point of attachment to maraviroc.

In other aspects, the linker is where n ranges from 0 to 12 (i.e. is 0, 1, 2, 3, 4, 5, 6, 7, 8, 9, 10, 11, or 12); * indicates the point of attachment to naltrexone; and ** indicates the point of attachment to maraviroc.

In other aspects, the linker is where n ranges from 0 to 12 (i.e. is 0, 1, 2, 3, 4, 5, 6, 7, 8, 9, 10, 11, or 12); * indicates the point of attachment to naltrexone; and ** indicates the point of attachment to maraviroc.

Assays: Use of the Bivalent Ligands as Probes

In some aspects, the novel bivalent ligands described herein are used as probes in order to detect, study and/or characterize of the interactions of the MOR and the CCR5 receptor. The probes are used for investigating the presence and role of e.g. MOR-CCR5 heterodimers in a number of diseases, including but not limited to: HIV, neuro-disorders, neuro-AIDS, neurodegradation, dementia, multiple sclerosis, neuropathic pain, chronic pain, brain cancers, etc.

In some aspects, this type of method is performed in vitro, e.g. in a laboratory that is studying HIV infection of cells, MOR-CCR5 heterodimers in a neurological disease or condition, etc. For example, the methods may be used in a diagnostic or investigative laboratory that assesses/evaluates samples obtained from subjects. In some aspect, the subjects are infected with HIV or at risk of being infected with HIV and/or are users of opioids. In other aspects, the subjects have or are suspected or at risk of having a neurological disorder. Alternatively, the samples may be from e.g. cell lines, tissue culture cells, artificial organoids, etc. Thus, the probes may be used for scientific investigation, to diagnose a disease in a subject, and/or to follow the course/development of a disease and/or to monitor the effects of treating the disease.

In some aspects, the methods are in vitro methods and comprise obtaining a sample, which may be a biological sample, and contacting the sample with at least one bivalent ligand as disclosed herein, under conditions and for a period of time sufficient to permit the at least one bivalent ligand to bind to MOR-CCR5 heterodimers that are present in the sample. If MOR-CCR5 heterodimers are present in the sample, the bivalent ligands will bind to and form complexes with the heterodimers.

Typically, the bivalent ligands are used to probe for the presence of heterodimers. However, since the two pharmacophores, naltrexone and maraviroc, are antagonists of the receptors MOR and CCR5, the bivalent ligands can also be used to probe for the presence of the receptors separately. Alternatively, by labeling the two pharmacophores differently, it is possible to distinguish between bivalent ligand binding to a single receptor vs binding to a heterodimer in a single sample through, for example, radioligand binding assays, GPCR functional assays, e.g. GTPgS binding, calcium flux, cAMP binding, β-arrestin recruitment assays. In this way, a ratio of dimerized to un-dimerized receptors (or vice versa) can be determined.

A step of "contacting" typically involves mixing the sample with a plurality of at least one type of bivalent ligand as described herein, using methods that are known in the art, e.g. by pipetting, using ultrasonic blending, shaking during sample incubation, etc. The assay methods are generally performed in a carrier or buffer that mimics physiological conditions, e.g. with respect to pH, and generally the assays are conducted at physiological temperature, e.g. at or about 37° C. The buffer pH is generally in the range of from about 7.0 to about 8.0 and is more usually from about 7.35 to about 7.45, and preferably at about 7.40. Suitable buffering agents include but are not limited to: sodium phosphate, HEPES, ACES, CHES, MES, Bis-Tris, Bis-Tris Propane, ADA, PIPES, MOPSO, BES, MOPS, TES, DIPSO, MOBS, TAPSO, Tris HEPPSO, POPSO, TEA, EPPS, Tricine, etc.

In some aspects, "sample" or "biological sample" as used herein means any biological fluid or suspension of cell(s) or tissue from a subject. In one embodiment suitable samples for use in the methods and with the diagnostic compositions or reagents described herein are samples or suspensions which require minimal invasion for testing, e.g., total plasma or isolated immunoglobulin G (IgG). Other samples include blood samples, including whole blood, peripheral blood, or serum, as well as cerebrospinal fluid, serous fluid, saliva or urine, vaginal or cervical secretions, and ascites fluids or peritoneal fluid or any tissues containing HIV reservoirs. In another embodiment, a suitable sample for use in the methods described herein includes peripheral blood, more specifically peripheral blood mononuclear cells. In another embodiment, the samples are concentrated by conventional means.

Alternatively, especially for research purposes, the samples may be from an in vitro source, i.e., a "biological sample" may originate from an in vitro source such as cultured cell lines, cultured tissues, cultured organoids, etc.

In any case, the samples that are tested usually comprise cells which may contain (are suspected of containing) or are known to contain MOR-CCR5 heterodimers, or, alternatively, are known to not contain MOR-CCR5 heterodimers if the purpose is to establish a control or baseline.

In other aspects, the bivalent ligands are used as probes in vivo, i.e. in a subject or patient to whom they are administered in order to identify whether MOR-CCR5 heterodimers are present in the subject. The present bivalent ligands are advantageously capable of passing blood-brain-barrier and thus are especially useful for detecting MOR-CCR5 heterodimers in vivo in the brain and/or nervous system.

Following exposure of cells to the bivalent ligands (either in a sample or in a subject) binding of the bivalent ligands to MOR-CCR5 heterodimers in the sample or subject is generally detected using methods known in the art. For example, the bivalent ligands may be labeled with a detectable label prior to being used and it is the level or amount of detectable label that is detected/measured.

As used herein, the term "detectable label" means a reagent, moiety or compound capable of providing a detectable signal, depending upon the assay format employed. A label may be chemically attached to any atom of a bivalent ligand that is amenable to a chemical reaction to attach the ligand. In some aspects, a plurality of detectable labels are attached to a bivalent ligand. Generally, if multiple labels are attached, they differ from each other. For example, a first type of label can be attached to the naltrexone portion of the molecule and/or a second type of label can be attached to the maraviroc portion of the molecule, and/or a third type of label can be attached to the linker portion of the molecule. In some aspects, the first and/or second and/or third labels are all unique, i.e. they differ from one another. For example, they may differ with respect to the wavelength at which they are detected.

Such labels are capable, alone or in concert with other compositions or compounds, of providing a detectable signal. In one embodiment, useful labels include fluorescent compounds, fluorophores, radioactive compounds, magnetic labels, and/or elements. In one embodiment, a fluorescent detectable fluorochrome, e.g., fluorescein isothiocyanate (FITC), phycoerythrin (PE), allophycocyanin (APC), coriphosphine-O (CPO) or tandem dyes, PE-cyanin-5 or -7 (PC5 or PC7)), PE-Texas Red (ECD), PE-cyanin-5.5, rhodamine, PerCP, and Alexa dyes. Combinations of such labels, such as Texas Red and rhodamine, FITC+PE, FITC+PECyS and PE+PECy7, among others may be used depending upon assay method. Still other fluorescent protein labels include green or red fluorescent protein (GFP, RFP) and others. In another embodiment, the labels are desirably interactive to produce a detectable signal. The selection of a useful fluorescent protein label from among those commercially available is within the skill of the art.

In some aspects, the label is detectable visually, e.g. colorimetrically. A variety of enzyme systems operate to reveal a colorimetric signal in an assay, e.g., glucose oxidase (which uses glucose as a substrate) releases peroxide as a product that in the presence of peroxidase and a hydrogen donor such as tetramethyl benzidine (TMB) produces an oxidized TMB that is seen as a blue color. Other examples include horseradish peroxidase (HRP) or alkaline phosphatase (AP), and hexokinase in conjunction with glucose-6-phosphate dehydrogenase that reacts with ATP, glucose, and NAD+ to yield, among other products, NADH that is detected as increased absorbance at 340 nm wavelength. Still other label systems that may be utilized in the described methods and constructs are detectable by other means, e.g., colored latex microparticles in which a dye is embedded may be used in place of enzymes to provide a visual signal indicative of the presence of the labeled ligand or construct in applicable assays The selection and/or generation of suitable labels for use in labeling the ligand and/or any component of the polymer construct is within the skill of the art, provided with this specification. Other components of the compositions and methods described herein can also be detectably labeled.

In some aspects, the detectable label is a labeled antibody or fragment thereof, e.g. with specificity for a bivalent ligand or a bivalent ligand-MOR-CCR5 heterodimer complex as described herein. An "antibody or fragment" can be a monoclonal antibody, a synthetic antibody, a recombinant antibody, a chimeric antibody, a humanized antibody, a human antibody, a CDR-grafted antibody, a multispecific binding construct that can bind two or more targets, a dual specific antibody, a bi-specific antibody or a multi-specific antibody, or an affinity matured antibody, a single antibody chain or an scFv fragment, a diabody, a single chain comprising complementary scFvs (tandem scFvs) or bispecific tandem scFvs, an Fv construct, a disulfide-linked Fv, a Fab construct, a Fab' construct, a F(ab')2 construct, an Fc construct, a monovalent or bivalent construct from which domains non-essential to monoclonal antibody function have been removed, a single-chain molecule containing one $V_L$, one $V_H$ antigen-binding domain, and one or two constant "effector" domains optionally connected by linker domains, a univalent antibody lacking a hinge region, a single domain antibody, a dual variable domain immunoglobulin (DVD-Ig) binding protein or a nanobody. Also included in this definition are antibody mimetics such as affibodies, i.e., a class of engineered affinity proteins, generally small (~6.5 kDa) single domain proteins that can be isolated for high affinity and specificity to any given protein target, such as a bivalent ligand. An antibody fragment or antigen binding fragment of an antibody refers to a portion of an antibody that binds specifically to a target and may include a Fab, Fab', F(ab')2, Fv fragment, single-chain Fv (scFv), scFv-Igs, and other fragments or portions of an antibody that can bind specifically to a target. In some aspects, a target, e.g. cells which may contain MOR-CCR5 heterodimers, are exposed to a bivalent ligand as described herein and then to a labeled antibody/antibody fragment specific for the bivalent ligand. In this case, bound labeled antibody is detected as indicating the presence of heterodimers. Alternatively, a first antibody/ antibody fragment that is specific for the bivalent ligand but not labeled may be bound to the bivalent ligand and a labeled secondary ligand specific for the first antibody is then bound thereto and detected.

The detection of these labels is performed by methods known to those of skill in the art, e.g. by detecting fluorescence, colors, magnetism, etc., depending on the type of label that is used. However, if the heterodimers that are detected are on cells in vivo (e.g. in a subject or patient), then preferably non-invasive imaging methods are used. By non-invasive detection methods is meant without limitation an in vivo imaging scanner, such as (but not limited to) magnetic resonance spectroscopy/imaging (MRS/MRI), positron emission tomography (PET) and other technology/ imaging (MRS/MRI), positron emission tomography (PET) and other technology. However, depending upon the use of the labeled ligands, the detection or imaging method may be readily selected by one of skill in the diagnostic art.

Generally, an increase in detection of a detectable label compared to a control indicates the presence of the MOR-CCR5 heterodimer in the sample or subject. Those of skill in the art are familiar with controls for such purposes. The controls may be negative controls, e.g. comparisons to samples which are known to not contain MOR-CCR5 heterodimers; or a pool of subjects who do not have the disease that is being investigated (or treated). Alternatively, or in addition, the controls may be positive controls, e.g. comparisons to samples which are known to contain MOR-CCR5 heterodimers; or a pool of subjects who do have the disease that is being investigated (or treated). Generally, the increase in the amount (level, quantity, etc.) of label is at least about 2 to 1000 fold, such as about 2, 10, 50, 100, 200, 250, 300, 350, 400, 450, 500, 550, 600, 650, 700, 750, 800, 850, 900, 950 or 1000 fold (or more) compared to a negative control, with the caveat that the negative control is assigned a value that is not zero.

In particular, for in vivo probing, the results may be used to provide or confirm a diagnosis of a disease of interest, especially a neurological disorder that is characterized by the formation and/or presence of MOR-CCR5 heterodimers. Alternatively, the probes may be used to monitor the course of a disease or treatment by conducting an assay and repeating the assay at a later time and/or at multiple later times. For example, to monitor the course of treating a disease, at least one assay may be conducted before treatment and the assay is repeated at selected time intervals thereafter. Since the assays are used in diseases that are characterized by the presence of MOR-CCR5 heterodimers, a decrease in the level of MOR-CCR5 heterodimers after treatment can confirm that a treatment is working. Conversely, a finding that the level of MOR-CCR5 heterodimers is not decreasing or is increasing after treatment would indicate that the treatment has not been successful, and a decision to change the treatment can be made, e.g. to increase a dose of a medicament, to switch to a different medicament and/or to add another different medicament to the treatment.

In further aspects, the bivalent ligands disclosed herein are used to investigate, in vitro, viral entry into cells e.g. by HIV. Comparisons of the ability of HIV to infect various cells types under different conditions, in the presence of various agents, and/or using the different bivalent ligands disclosed herein can be made, e.g. to determine which agents or conditions are optimal for treating patients in vivo.

Methods of Treating and Preventing Diseases and Conditions

In further aspects, the bivalent ligands disclosed herein are used to prevent and/or treat a disease or condition that is characterized by, associated with, caused by, exacerbated by, etc. the formation of MOR-CCR5 heterodimers. One advantage of using the bivalent ligands as therapeutics to treat diseases is to avoid drug-drug interactions stemming from using two separate pharmacophores as drugs. For example, the basic property of naltrexone may influence the solubility and absorption of maraviroc. The molecular weight of such ligands could be an issue for the development of therapeutics. However, as discussed above for in vivo probing, the bivalent ligands disclosed herein are able to readily pass blood-brain-barrier.

The methods generally involve administering to a patient or subject in need thereof a therapeutically effective amount of at least one bivalent ligand as described herein. "Patient" or "subject" or "individual" as used herein means a mammalian animal, including a human, a veterinary or farm animal, a domestic animal or pet, and animals normally used for clinical research. In one embodiment, the subject of these methods and compositions is a human.

Diseases and conditions which may be prevented and/or treated by administering the bivalent ligands disclosed herein include but are not limited to: HIV, neuro-AIDS, dementia, neurodegradation, multiple sclerosis, neuropathic pain, chronic pain, brain cancers, etc.

Those of skill in the art will recognize that while the complete prevention or elimination of one or more symptoms of a disease is desirable, much advantage can accrue if this does not occur, but if disease progression is slowed, or if one or more symptoms are lessened, even if a total "cure" is not achieved.

In some aspects, the disease or condition is HIV. Accordingly, provided herein are methods of preventing the entry of HIV into a cell (e.g. a cell of or within a subject) by contacting the cell with a compound disclosed herein. In some aspects, the cell is a cell that is susceptible to infection (entry, invasion, etc.) by HIV. The methods generally involve contacting the cell with an amount of compound that is sufficient to bind to one or more of MOR, CCR5, and MOR-CCR5 heterodimers, and preferably to MOR-CCR5 heterodimers. Binding of the compounds blocks the receptors, especially the MOR-CCR5 heterodimer receptor complex, and prevents the virus from binding to the receptors and/or receptor complex. As a result, viral entry into the cell, which is typically exacerbated or accelerated by opioid binding, is prevented.

In one embodiment, the subject is a human not diagnosed with HIV infection. In other embodiments, the subject is an HIV-infected subject who is symptomatic or non-symptomatic. In another embodiment, the subject is a human who has received, or is receiving, anti-retroviral therapy (ART). In another embodiment, the subject is a human who has discontinued ART. For diagnostic purposes, the subject may a healthy subject.

The subject may be an opioid user, either for legitimate medical purposes or as a recreational drug. The opioid may be any of the following:

A natural opiate. Natural opiates are alkaloids, nitrogen-containing base chemical compounds that occur in plants such as the opium poppy. Natural opiates include morphine, codeine, and thebaine (paramorphine).

A semi-synthetic opioid. Semi-synthetic/humanmade opioids are created in labs from natural opiates. Semi-synthetic opioids include hydromorphone, hydrocodone, and oxycodone. Semi-synthetic opioids also include the illegal Schedule I drug, heroin, which is made from morphine.

A fully synthetic opioid. Fully synthetic/humanmade opioids such as fentanyl, pethidine, levorphanol, methadone, tramadol, and dextropropoxyphene are devoid of natural opiates.

In some aspects, the opioid that is used by the subject is an opioid that binds to MOR, examples of which include but are not limited to: morphine, heroin, fentanyl oxycodone, oxymorphone, hydrocodone, hydromorphone, etc.

In some aspects, the subject is a subject being treated for HIV who is also in need of treatment with an opioid. In other aspects, the subject is an opioid user (e.g. an addict) who is at risk of contracting HIV, e.g. through needle sharing, sexual contact, etc.

In other aspects, methods of preventing opioid exacerbation of HIV entry into cells (cells that are susceptible to infection by HIV) is provided. Generally, the methods involve contacting the cells with an amount of at least one compound disclosed herein sufficient to bind to one or more of MOR, CCR5, and MOR-CCR5 heterodimers. Binding prevents opioid exacerbation of HIV entry into cells. Such methods may be conducted in vitro or in vivo.

In other aspects, methods of preventing opioid accelerated HIV invasion of cells are provided. Generally, the methods involve contacting the cells with an amount of at least one compound disclosed herein sufficient to bind to one or more of MOR, CCR5, and/or MOR-CCR5 heterodimers. Binding prevents opioid exacerbation of HIV entry into cells. Such methods may be conducted in vitro or in vivo.

Pharmaceutical Compositions

The compounds described herein are generally delivered (administered) as a pharmaceutical or therapeutic composition. Such pharmaceutical compositions generally comprise at least one of the disclosed compounds, i.e. one or more than one (a plurality) of different compounds may be included in a single formulation. Accordingly, the present invention encompasses such formulations/compositions. The compositions generally include one or more substantially purified compounds as described herein, and a pharmacologically suitable (physiologically compatible) carrier. In some aspects, such compositions are prepared as liquid solutions or suspensions, or as solid forms such as tablets, pills, powders and the like. Solid forms suitable for solution in, or suspension in, liquids prior to administration are also contemplated (e.g. lyophilized forms of the compounds), as are emulsified preparations. In some aspects, the liquid formulations are aqueous or oil-based suspensions or solutions. In some aspects, the active ingredients are mixed with excipients which are pharmaceutically acceptable and compatible with the active ingredients, e.g. pharmaceutically acceptable salts. Suitable excipients include, for example, water, saline, dextrose, glycerol, ethanol and the like, or combinations thereof. In addition, a composition may contain minor amounts of auxiliary substances such as wetting and/or emulsifying agents, pH buffering agents, preservatives, and the like. In some aspects, it is desired to administer an oral form of the composition so various thickeners, flavorings, diluents, emulsifiers, dispersing aids or binders and the like are added. The compositions of the present invention may contain any such additional ingredients so as to provide the composition in a form suitable for administration. The final amount of compound in the formulations varies but is generally from about 1-99%. Still other suitable formulations for use in the present invention are found, for example in Remington's Pharmaceutical Sciences, 22nd ed. (2012; eds. Allen, Adejarem Desselle and Felton).

Some examples of materials which can serve as pharmaceutically acceptable carriers include, but are not limited to, ion exchangers, alumina, aluminum stearate, lecithin, serum proteins (such as human serum albumin), buffer substances (such as Tween® 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions. In addition, other non-toxic compatible lubricants such as sodium lauryl sulfate and magnesium stearate, as well as coloring agents, releasing agents, coating agents, sweetening, flavoring and perfuming agents, preservatives and antioxidants may also be present in the composition, according to the judgment of the formulator.

"Pharmaceutically acceptable salts" refers to the relatively non-toxic, inorganic and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulfamates, malonates, salicylates, propionates, methylene-bis-.beta.-hydroxynaphthoates, gentisates, isethionates, di-p-toluoyltartrates, methanesulfonates, ethanesulfonates, benzenesulfonates, p-toluenesulfonates, cyclohexylsulfamates and laurylsulfonate salts, and the like. See, for example S. M. Berge, et al., "Pharmaceutical Salts," J. Pharm. Sci., 66, 1-19 (1977) which is incorporated herein by reference. Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are generally preferred. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which have sufficient basicity to form a stable salt, and preferably include those amines which are frequently used in medicinal chemistry because of their low toxicity and acceptability for medical use, examples of which include but are not limited to: ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, and dicyclohexylamine, and the like.

Administration

The compounds are administered in vivo by any suitable route including but not limited to: inoculation or injection (e.g. intravenous, intraperitoneal, intramuscular, subcutaneous, intra-aural, intra-articular, intra-mammary, and the like); topical application; by absorption through epithelial or mucocutaneous linings (e.g., nasal, oral, vaginal, rectal, gastrointestinal mucosa, and the like); orally; and by inhalation (e.g. as a mist or spray). Formulations suitable for a particular mode of administration are also encompassed, e.g. pills, capsules, liquids, etc. for oral administration; creams, ointments and suppositories for intravaginal or rectal administration; as eye drops for administration to the eye; etc. In some aspects. In preferred embodiments, the mode of administration is oral or by injection, e.g. intravenous.

The compositions may be administered in conjunction with other treatment modalities such as but not limited to: opioids, synthetic analgesics such as methadone, substances that boost the immune system, various chemotherapeutic agents, antibiotic agents, pain medication, HIV antiviral "cocktails", and the like.

Kits

In further aspects, kits for detecting a MOR-CCR5 heterodimer are provided. The kits typically include at least one bivalent ligand as disclosed herein, and may include a plurality of bivalent ligands, e.g. from about 2-100 or more. The bivalent ligands may be labeled with a detectable label (i.e. prelabeled prior to packaging) or unlabeled (i.e. the end-user can attach a label if wanted). If the bivalent ligands are unlabeled, the kits may include detectable labels which can be attached to the bivalent ligands by the user. The bivalent ligands may be present in the kit in a solution, for example, in a biocompatible carrier (medium) as described elsewhere herein and may be labeled to indicate the concentration of the bivalent ligands. Alternatively, the bivalent ligands may be in a dehydrated or lyophilized form that can be reconstituted (e.g. hydrated, solubilized, dissolved, suspended, etc.) by the end user, e.g. in a bottle, tube ampule or other container. Preparations of bivalent ligands that are dehydrated, (e.g. lyophilized) are encompassed by the present disclosure, as are forms of the bivalent ligands in which they are solubilized in a carrier, e.g. in a bottle, tube, ampule or other container. Thus, containers for containing either dehydrated forms of the bivalent ligands or hydrated forms of the bivalent ligands, the containers being packaged by methods know in the art, are also encompassed by this disclosure. The kits of the disclosure typically also include standards or controls, e.g. samples of bivalent ligands of known concentration and/or samples of MOR-CCR5 heterodimers of known concentration. For example, cells comprising known amounts of MOR-CCR5 heterodimers may be included, either in a sterile buffer or e.g. in lyophilized form, in suitable containers and packaging. An insert with instructions for use is generally also included in a kit.

It is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

EXAMPLES

Example 1. Synthesis of the First Series of Bivalent Ligands

Herein, the structure-based molecular design, synthesis, and comprehensive biological investigations of a novel bivalent ligand VZMC013, are reported. The molecular properties of VZMC013 are significantly improved compared to prior art bivalent ligands.
Structure-Based Molecular Design.

The crystal structure of the MOR in complex with an epoxymorphinan antagonist (3-funaltrexamine has been determined and showed that the C6-position of β-FNA in the co-crystal structure pointed toward the extracellular end of transmembrane helix 5 (TM5) and TM6 of the MOR.

Figures 1A, 1B, 1C:
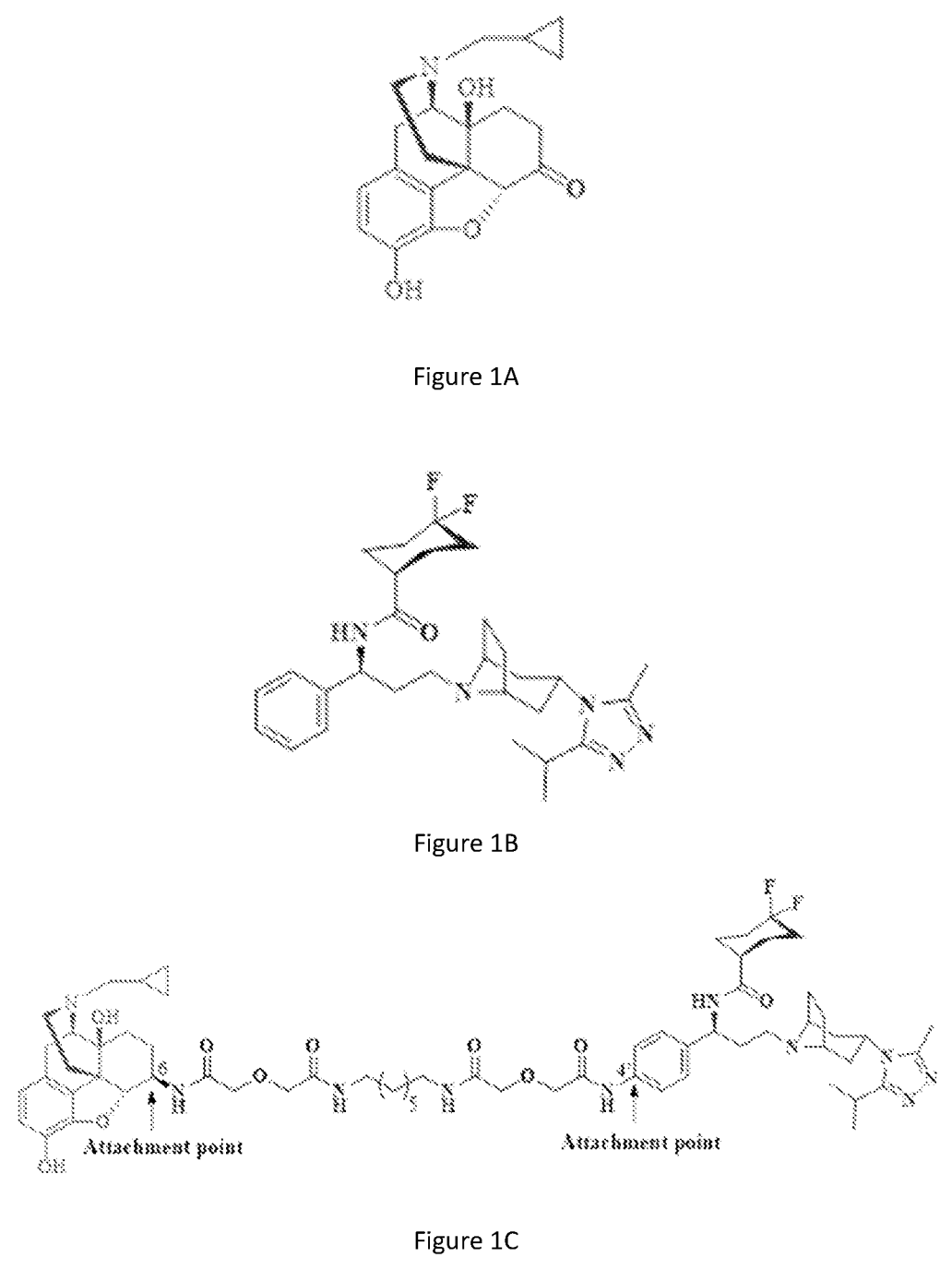

Considering the high structural similarity between naltrexone and β-FNA, the C6-position of naltrexone was selected as the attachment point on the MOR pharmacophore. The crystal structure of CCR5 complexing with maraviroc had been determined and showed that maraviroc bound within the pocket such that the 3'-methyl group on the 1,2,4-triazol moiety is directed away from the extracellular domains of TM 1, 2, and 3. Thus, the 3'-methyl group on the 1,2,4-triazol moiety (rather than the 4'-position of the phenyl ring as used in the prior art ligand (FIG. 1C) was selected as the attachment point for the CCR5 pharmacophore.

With both attachment points designated, a 21-atom length spacer was used to construct the novel bivalent ligand, VZMC013. To further investigate how the spacer length affects biological activities, two additional bivalent ligands, VZMC017 and VZMC019 were synthesized:

VZMC013 where n is 5,
VZMC017 where n is 7,
and VZMC019 where n is 3.

A new CCR5 monovalent control VZMC014 (containing the CCR5 antagonist pharmacophore only) was synthesized as a control as were new CCR5 monovalent controls VZMC018 and VZMC020 (controls for VZMC017 and VZMC019, respectively).

n = 5, VZMC014 (newly synthesized)
n = 7, VZMC018 (newly synthesized)
n = 3, VZMC020 (newly synthesized)

The MOR monovalent control ligand VZMC002

VZMC002

(previously reported)

Figures 1D, 1E:
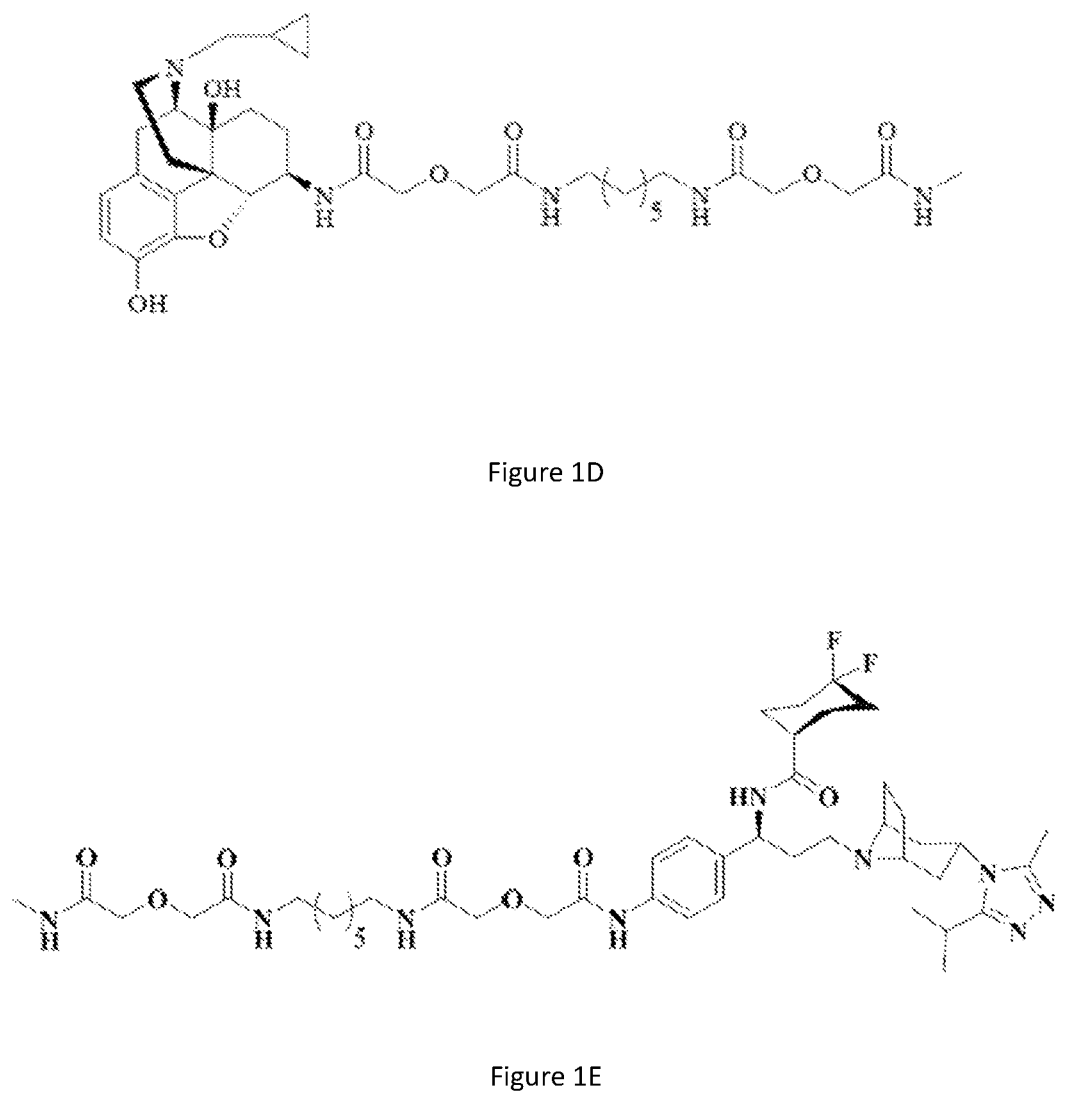

(see also FIG. 1D) was adopted from a previous study.

The synthetic routes for these compounds are depicted in Schemes 1-5. Synthesis of the 2'-aminoethyl maraviroc precursor 24 was first carried out step-wisely (Schemes 1-3).

First, to prepare compound 9, a similar synthetic route as reported was employed (Scheme 1). The benzaldehyde 3 was condensed with ammonium acetate and malonic acid to yield the amino acid 4, which was esterified in methanol to give β-amino ester 5. The racemic β-amino ester 5 was resolved by using L-(+)-tartaric acid to afford 6 as the L-(+)-tartaric acid salt. Protection of 6 using benzyl chloroformate was carried out under modified Schotten-Baumann conditions, followed by hydrolysis to furnish the Cbz-protected acid 7. The β-aminoaldehyde 9 was obtained from 7 through borane-mediated reduction and subsequent oxidation of the resulting alcohol under Parikh-Doering conditions. Then, commercially available β-alanine 10 was converted to corresponding methyl ester hydrochloride 11, which was protected using fluorenylmethyloxycarbonyl-chloride (Fmoc-Cl) to provide 12. Hydrazinolysis of 12 led to the Fmoc-protected hydrazide 13 (Scheme 2).

-continued

7

8

9

*a*Reagents and conditions: (a) malonic acid (1.5 equiv), ammonium formate (2.5 equiv), EtOH, reflux, 59%; (b) i) Conc. $H_2SO_4$, MeOH, 0° C. to r.t.; ii) 2M NaOH, pH 10, 0° C. Two steps 99%; (c) L-(+)-tartaric acid (1 equiv), MeOH, 45° C. to r.t., 25%; (d) i) benzyl chloroformate (1.2 equiv), $Na_2CO_3$(aq) (3.3 equiv), dichloromethane, 0° C. to r.t.; ii) 2M NaOH, pH 13, MeOH, 0° C. to r.t.; iii) 2M HCl, pH 1, 0° C. Three steps 80%; (e) $BH_3$·THF (4 equiv), anhydrous THF, $N_2$, 0° C. to r.t., 58%; (f) sulfur trioxide pyridine complex (5 equiv), $Et_3N$ (10 equiv), DMSO/dichloromethane=1/1, 0° C., 87%.

Scheme 1. Synthesis of intermediate 9

3

4

5

6

Scheme 2. Synthesis of intermediate 13*a*

10

11

12

-continued

-continued

13

16

17

18

19

20

21

*Reagents and conditions: (a) thionyl chloride (2.5 equiv), MeOH, 0° C. to r.t., 62%; (b) Fmoc-Cl (1.05 equiv), Et$_3$N (3.75 equiv), dichloromethane, 0° C. to r.t., 81%; (c) hydrazine monohydrate (5 equiv), MeOH, r.t., 49%.

Next, N-benzylnortropinone 15 was obtained from acetonedicarboxylic acid 14, tetrahydro-2,5-dimethoxyfuran, and benzylamine following the literature procedures, and was then transformed to oxime 16 using hydroxylamine hydrochloride. The oxime 16 was reduced by sodium in n-pentanol to give amine 17. Acylation of 17 with isobutyryl chloride supplied the subunit 18. Activation of 18 to its corresponding imidoyl chloride followed by trapping with hydrazide 13 and acetic acid-catalyzed thermal cyclization in three successive steps provided the triazole 19. Subsequent Bn-deprotection of compound 19 by hydrogenolysis with p-toluenesulfonic acid (p-TsOH) and 30% Pd/C afforded the key intermediate 20, which was directly used as a tosylate salt for the next step. Reductive amination of amine 20 with the β-aminoaldehyde 9 was facilitated using sodium triacetoxyborohydride as a reducing reagent to give compound 21. Removal of the Cbz group of 21 by hydrogenolysis with 30% Pd/C in methanol offered free amine 22, which was then coupled with the 4,4-difluorocyclohexanecarboxylic acid to yield amide 23. Treatment of 23 in 20% piperidine/DMF finally provided the precursor 2'-aminoethyl maraviroc 24 (Scheme 3).

Scheme 3. Synthesis of 2'-aminoethyl maraviroc precursor (24)$^a$

14

15

53

-continued

22

23

54

-continued

24

$^a$Reagents and conditions: (a) tetrahydro-2,5-dimethoxyfuran (1 equiv), benzyl amine (1.2 equiv), NaOAc, HCl(aq), 0° C. to r.t., 48%; (b) hydroxylamine hydrochloride (1 equiv), pyridine (1.1 equiv), EtOH, reflux, 51%; (c) sodium (10 equiv), n-pentanol,120° C., 72%; (d) isobutyryl chloride (1.2 equiv), Na2CO3(aq) (2.8 equiv), dichloromethane, 0° C. to r.t., 49%; (e) i) PCl$_5$ (1.5 equiv), dichloromethane, 0° C.; ii) 13 (0.77 equiv), tert-amyl alcohol, 0° C. to r.t.; iii) AcOH, tert-amyl alcohol, 85° C. Three steps 29%; (f) p-TsOH monohydrate (1 equiv), 30% Pd/C, MeOH, 60 psi H$_2$, r.t.; (g) 9 (1.1 equiv), NaBH(OAc)3 (1.1 equiv), AcOH, dichloromethane, r.t. Two steps 53%; (h) 30% Pd/C, MeOH, 60 psi H$_2$, r.t., 67%; (i) 4,4-difluorocyclohexanecarboxylic acid (2 equiv), EDCI (2 equiv), HOBt (2 equiv), Et$_3$N (4 equiv), 4Å molecular sieves (MS), dichloromethane, 0° C. to r.t., 54%; (j) 20% piperidine/DMF, r.t, 42%.

With intermediate 24 in hand, we sought to synthesize the naltrexamine-containing acids 30a-c to prepare the bivalent ligands as previously reported, with only minor modifications. The bivalent ligands VZMC013, VZMC017 and VZMC019 were obtained by coupling amine 24 with corresponding acids 30a-c via HOBt/EDCI method (Scheme 4). In addition, the monovalent ligands VZMC014, VZMC018 and VZMC020 were furnished following similar synthetic protocols (Scheme 5).

Scheme 4. Synthesis of the bivalent ligands VZMC013, VZMC017 and VZM019$^a$ 25a, n = 5,
25b, n = 7,
25c, n = 3, 26a, n = 5,
26b, n = 7,
26c, n = 3, 27a, n = 5,
27b, n = 7,
27c, n = 3, 6β-naltrexamine -continued 28a, n = 5,
28b, n = 7,
28c, n = 3, d →

29a, n = 5,
29b, n = 7,
29c, n = 3, e →

30a, n = 5,
30b, n = 7,
30c, n = 3, 24
f
→

-continued

VZMC013, n = 5,
VZMC017, n = 7,
VZMC019, n = 3,

[a]Reagents and conditions: (a) benzyl chloroformate (1 equiv), dichloromethane/MeOH = 1/1, 0° C. to r.t., 30%-49%; (b) diglycolic anyhydride (1.05 equiv), THF, r.t., 70%-86%; (c) 6β-naltrexamine hydrochloride (0.5 equiv), EDCI (1.25 equiv), HOBt (1.05 equiv), Et₃N (2 equiv), 4Å MS, anhydrous DMF, 0° to r.t., 36%-61%; (d) 30% Pd/C, MeOH, 60 psi H₂, r.t., 90%-94%; (e) dyglycolic anhydride (1 equiv), DMF, r.t., 72%-81%; (f) 24 (1.2 equiv), EDCI (4 equiv), HOBt (4 equiv), Et₃N (4 equiv), 4Å MS, anhydrous DMF, 0° to r.t., 20%-55%.

Scheme 5. Synthesis of the monovalent ligands VZMC014, VZMC018 and VZMC020[a]

26a, n = 5,
26b, n = 7,
26c, n = 3, 32a, n = 5,
32b, n = 7,
32c, n = 3, 33a, n = 5,
33b, n = 7,
33c, n = 3, 34a, n = 5,
34b, n = 7,
34c, n = 3,

-continued

VZMC014, n = 5,
VZMC018, n = 7,
VZMC020, n = 3,

[a]Reagents and conditions: (a) 31 (1.2 equiv), EDCI (1.5 equiv), HOBt (1.2 equiv), Et₃N (2 equiv), 4Å MS, anhydrous DMF, 0° C. to r.t., 27%-47%; (b) 10% Pd/C, MeOH, 60 psi H₂, r.t. 69%-100%; (c) diglycolic anhydride (1 equiv), DMF, r.t., 92%-100%; (d) 24 (1.2 equiv) EDCI (4 equiv), HOBt (4 equiv), Et3N (4 equiv), 4Å MS, anhydrous DMF, 0° C. to r.t., 21%-46%.

In vitro MOR radioligand binding studies. All bivalent ligands were first tested for their binding affinity to the MOR. The competitive radioligand binding assay was conducted using monoclonal mouse MOR expressed in CHO cell lines (mMOR-CHO). VZMC013 showed high MOR binding affinity ($K_i$ value of 6.05 nM; Table 1), which was 8.6-fold higher than that of VZMC001 ($K_i$=51.8 nM), suggesting that the structure-based re-selection of the attachment point on the CCR5 pharmacophore exerted partial influence on MOR binding as well. Moreover, VZMC013 possessed relatively higher binding affinity than that of VZMC017 ($K_i$=11.2 nM), while similar to that of VZMC019 ($K_i$=4.23 nM), indicating that the chosen spacer length range was suitable to preserve ligand binding affinity to the MOR. The monovalent ligand VZMC002 displayed a slightly lower MOR affinity compared to VZMC013 (Table S1). VZMC013 possessed relatively lower binding affinity for the MOR compared to the parent pharmacophore naltrexone ($K_i$=0.7 nM), which was not unusual based on previous reports from other research groups. Briefly, VZMC013 effectively recognized the MOR.

TABLE 1

MOR Radioligand Binding Affinity.[a]

| Compounds | Ki (nM) |
| --- | --- |
| VZMC013 | 6.05 ± 0.22[b] |
| VZMC017 | 11.2 ± 1.92[b] |
| VZMC019 | 4.23 ± 0.27[b] |
| VZMC001 | 51.8 ± 7.9[c] |
| Naltrexone | 0.7 ± 0.1[c] |

[a][³H]naloxone was used as the radioligand in the binding assay.

[b]The values are the mean ± SEM of at least three independent experiments.

[c]Data have been reported and are presented here for comparison.

TABLE S1

MOR radioligand binding affinity.

| Compounds | Ki (nM) |
| --- | --- |
| VZMC002 | 9.2 ± 3.4[a] |
| Naltrexone | 0.7 ± 0.1[a] |

[a]Data have been reported in Reference 1, and are presented here for comparison.

MOR [³⁵S]GTPγS functional studies. The [³⁵S]GTPγS functional assay was carried out in mMOR-CHO cells to define the relative efficacy of these bivalent ligands to activate the MOR as previously illustrated. $E_{max}$ values of all ligands were measured relative to that of the maximal stimulated response produced by the full MOR agonist DAMGO. VZMC013 produced minimal stimulation of the MOR and displayed insignificant apparent efficacy (% $E_{max}$=9.22%), similar to those of the previously designed bivalent ligand VZMC001 and the parent compound naltrexone (Table 2). VZMC017 also showed minimal efficacy (% $E_{max}$=4.27%) whereas VZMC019 exhibited slightly higher efficacy (% $E_{max}$=19.4%) but was still a low-efficacy partial agonist relative to DAMGO. Overall, the results indicated that VZMC013 may act as an MOR antagonist as designed, comparable to the MOR neutral antagonist naltrexone.

TABLE 2

[³⁵S]GTPγS Binding Results.

| Compounds | % $E_{max}$ of DAMGO |
| --- | --- |
| VZMC013 | 9.22 ± 0.94[a] |
| VZMC017 | 4.27 ± 0.66[a] |
| VZMC019 | 19.4 ± 1.94[a] |
| VZMC001 | 11.7 ± 1.2[b] |
| Naltrexone | 7.75 ± 0.20[c] |

[a]The values are the mean ± SEM of at least three independent experiments.

[b]Data have been reported and are presented here for comparison.

[c]Data have been reported and are presented here for comparison.

Calcium mobilization assay results in mMOR-CHO cells. The pharmacological profiles of the three newly prepared MOR bivalent ligands were further characterized for their effects on MOR-dependent intracellular $Ca^{2+}$ signaling in an mMOR-CHO cell line that was transfected with chimeric Gqi5 protein as previously described. No agonism was observed for VZMC013 at varying concentrations, compared with the known MOR agonist DAMGO ($EC_{50}$=36.3±1.85 nM). Meanwhile, VZMC013 inhibited DAMGO-induced increases in intracellular $Ca^{2+}$ concentration [$Ca^{2+}$]i effectively with moderate potency (Table 3).

Additionally, VZMC013 showed comparable potency to the previously developed bivalent ligand VZMC001 ($IC_{50}$=40.0 nM) in inhibiting DAMGO-stimulated $Ca^{2+}$ mobilization which conformed to our molecular design. Moreover, VZMC013 was more potent than VZMC017 ($IC_{50}$=74.4 nM) and VZMC019 ($IC_{50}$=1103 nM), further suggesting the critical role of spacer length in designing bivalent ligands. In summary, the results of the [$^{35}$S]GTPγS functional assay and the ability to inhibit DAMGO-stimulated calcium mobilization demonstrated that VZMC013 is a potent MOR antagonist.

TABLE 3

Inhibition of DAMGO Induced $Ca^{2+}$ Mobilization.

| Compounds | $IC_{50}$ (nM) |
|---|---|
| VZMC013 | 50.0 ± 2.45[a] |
| VZMC017 | 74.4 ± 3.20[a] |
| VZMC019 | 1103 ± 7.11[a] |
| VZMC001 | 40.0 ± 4.8[b] |
| Naltrexone | 6.62 ± 1.45[c] |

[a]The values are the mean ± SEM of at least three independent experiments.
[b]Data have been reported and are presented here for comparison purposes.

In vitro CCR5 radioligand binding studies. To verify the binding affinity of the bivalent ligands to the CCR5, the competitive radioligand binding assay was conducted in recombinant rhesus macaque CCR5-expressing Chem-1 cells, and macrophage inflammatory protein 1 beta (MIP-1β) was used as a control. VZMC013 exhibited a reasonably high binding affinity with a Ki value of 3.29 nM (Table 4), which was 12-fold greater than the monovalent compound VZMC014 ($K_i$=41 nM) (Table S2). In addition, VZMC013 possessed a relatively higher binding affinity for the CCR5 than VZMC017 and VZMC019. Most importantly, VZMC013 showed a dramatically improved binding affinity for the CCR5 than VZMC001, demonstrating the success of the attachment point relocation on the CCR5 pharmacophore via the structure-based molecular design approach.

TABLE 4

CCR5 Radioligand Binding Affinity.[a]

| Compounds | Ki (nM)[b] |
|---|---|
| VZMC013 | 3.29 ± 0.29 |
| VZMC017 | 5.70 ± 0.23 |
| VZMC019 | ND[c] |
| VZMC001 | 239 ± 56[d] |
| MIP-1β | 0.056 ± 0.006 |

[a][$^{125}$I]MIP-1α was used as the radioligand in the binding assay.
[b]$K_i$ values were calculated using the Cheng-Prusoff equation. The values are the mean ± SEM of at least three independent experiments.
[c]Its $IC_{50}$ value is higher than 10,000 nM, the highest concentration tested.
[d]Data have been reported and are presented here for comparison. It should be noted that the assay methods were similar with only minor differences.

TABLE S2

CCR5 radioligand binding affinity.[a]

| Compounds | Ki (nM)[b] |
|---|---|
| VZMC014 | 41 ± 1 |
| VZMC018 | 7.15 ± 0.26 |
| VZMC020 | ND[c] |
| MIP-1β | 0.056 ± 0.006 |

[a][$^{125}$I]MIP-1α was used as the radioligand in the binding assay.
[b]$K_i$ values were calculated using the Cheng-Prusoff equation. The values are the mean ± SEM of at least three independent experiments.
[c]Not determined.

Calcium mobilization assay results in HOS-CCR5 cells. We then conducted the calcium mobilization assay to further test both the agonist and antagonist properties of the newly synthesized compounds in the HOS-CCR5 (stably transfected for the expression of CCR5) cells using our reported protocol, as calcium mobilization is associated with the activation of CCR5. Prior to the assay, the HOS-CCR5 cells were transiently transfected with a Gqi5 to boost calcium signaling levels. As expected, none of these compounds appeared to activate CCR5 within the range of concentrations tested (represented by VZMC013 and VZMC014,) compared to the control C—C motif chemokine ligand 5 (CCL5/RANTES) under the same conditions (CCL5 exhibited an agonism profile with an $EC_{50}$ value of 155±6.58 nM).

In the antagonism assay, these compounds were assessed for their ability to inhibit CCL5-stimulated $Ca^{2+}$ mobilization. As shown in Table 5, VZMC013 demonstrated two-digit nanomolar inhibitory potency ($IC_{50}$=57.5 nM) and was 2.2-fold more potent than VZMC001 ($IC_{50}$=126 nM). Thus, as predicted, the positional switch in the spacer attachment on maraviroc in VZMC013 improved its inhibition of CCR5 agonist-induced calcium mobilization relative to VZMC001. This prediction was further supported by the enhanced potency of VZMC014 ($IC_{50}$=116 nM) compared to the monovalent ligand VZMC003 (FIG. 1E) ($IC_{50}$=622 nM)33 (Table S3). VZMC013 also demonstrated much higher potency than those of VZMC017 and VZMC019, indicating the importance of spacer length. In brief, VZMC013 acted as a potent CCR5 antagonist.

TABLE 5

Inhibition of CCL5-stimulated Intracellular $Ca^{2+}$ Mobilization.[a]

| Compounds | $IC_{50}$ (nM) |
|---|---|
| VZMC013 | 57.5 ± 4.87 |
| VZMC017 | 965 ± 30.5 |
| VZMC019 | 1260 ± 77.6 |
| VZMC001 | 126 ± 28[b] |
| Maraviroc | 0.77 ± 0.20 |

[a]The values are the mean ± SEM of at least three independent experiments.
[b]Data have been reported and are presented here for comparison purposes.

TABLE S3

Inhibition of CCL5-stimulated intracellular $Ca^{2+}$ mobilization.[a]

| Compounds | $IC_{50}$ (nM) |
|-----------|----------------|
| VZMC014 | 116 ± 2.53 |
| VZMC018 | 39.6 ± 4.01 |
| VZMC020 | 919 ± 45.4 |
| VZMC003 | 622 ± 36[b] |
| Maraviroc | 0.77 ± 0.20 |

[a]The values are the mean ± SEM of at least three independent experiments.
[b]Data have been reported and are presented here for comparison purposes.

Anti-HIV-1BaL activity and cytotoxicity of VZMC013 in GHOST CCR5 cells. To further characterize the capacity of VZMC013 to block HIV-1 entry by occupying the HIV binding site on the CCR5, we utilized a well-established HIV-1 entry assay, in which the ability for small molecules to inhibit HIV-1 entry is measured as a decrease in HIV-1 reverse transcriptase (RT) activity that is equal to a decrease in radioactivity output after standard radioactive incorporation of tritiated thymidine triphosphate (needed for the synthesis of viral DNA). This assay was run in GHOST-CCR5 cells using the CCR5-tropic viral strain HIV-1BaL. Compounds VZMC001, VZMC002, VZMC013, and VZMC014 (maraviroc tested as the control) were subjected to this assay. The treatment concentrations for each compound were 0 and from 0.001 to 100 µM; in which the RT activity at 0 µM of tested compound was defined as 100% and the results were expressed as $EC_{50}$ values. As shown in Table 6, the previously developed bivalent ligand VZMC001 did not show any significant inhibition of HIV-1 entry at concentrations up to 100 µM (RT activity: 107.6% to 226.1%), whereas the newly designed bivalent ligand VZMC013 acted as a potent inhibitor in preventing HIV-1 entry, with an $EC_{50}$ value of 0.093 µM. The results from this assay clearly indicated that our structure-based design strategy has yielded a bivalent ligand with a markedly improved ability to inhibit HIV-1 entry in cells compared to the previously designed bivalent compound, and the proper selection of an attachment site on the CCR5 pharmacophore was critical for inhibiting HIV-1 entry.

These compounds were concurrently assessed for cytotoxicity in GHOST-CCR5-expressing cells using the XTT assay. The treatment concentrations for each compound were the same as in the anti-HIV assay in which the viability of untreated cells was defined as 100%, and the results were interpreted as $TC_{50}$ (a 50% reduction in cell viability). The therapeutic index (TI, $TC_{50}/EC_{50}$) values were calculated if applicable. As depicted in Table 6 and Table S4, neither VZMC013 nor other compounds exhibited cytotoxicity at any concentration ≤100 µM (cell viability ~100%). The bivalent ligand VZMC013 possessed a TI value greater than 1075.

TABLE 6

Inhibition of HIV-1$_{BaL}$ and Cytotoxicity in GHOST CCR5 Cells.[a]

| Compounds | $EC_{50}$ (µM) | $TC_{50}$ (µM) | TI |
|-----------|----------------|----------------|-----|
| VZMC013 | 0.093 ± 0.004 | >100 | >1075 |
| VZMC001 | >100 | >100 | — |
| Maraviroc | 0.018 ± 0.002 | >0.5 | >28 |

[a]Measured in triplicate.

TABLE S4

Inhibition of HIV-1$_{BaL}$ and cytotoxicity in GHOST CCR5 cells.[a]

| Compounds | $EC_{50}$ (µM) | $TC_{50}$ (µM) | TI |
|-----------|----------------|----------------|-----|
| VZMC014 | 2.62 ± 1.25 | >100 | >38 |
| VZMC002 | >100 | >100 | — |
| Maraviroc | 0.018 ± 0.002 | >0.5 | >28 |

[a]Measured in triplicate

Figure 3A:
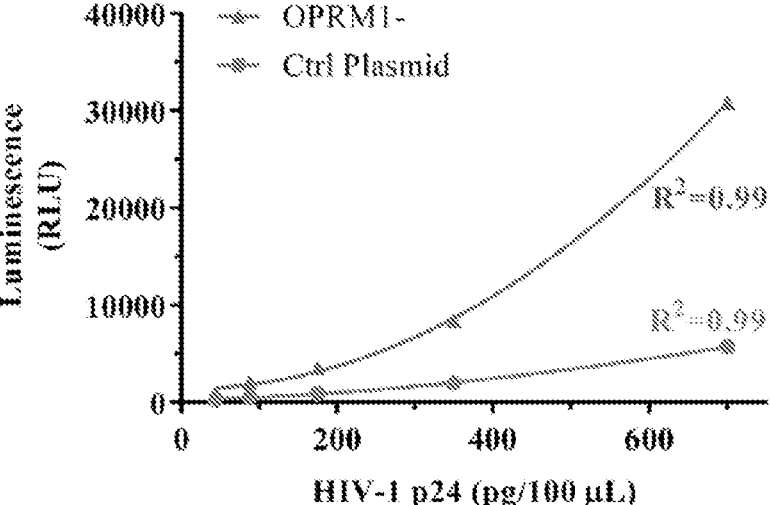
FIG. 3A-D. A: comparison of intracellular concentration of HIV-1BaL (RLU) in OPRM1- and control plasmid transfected TRM-b1 cells; B-D: Comparison of % inhibition of infection by VZMC013 in control plasmid (A), OPRM1 (B), and OPRM1 (C, with 100 μM of morphine added)-transfected TZM-b1 cells. % inhibition of infection was related to the decrease of relative luminescence units (RLU). Data analysis was performed using GraphPad Prism version 8.0.1 for Windows.
Figure 3B:
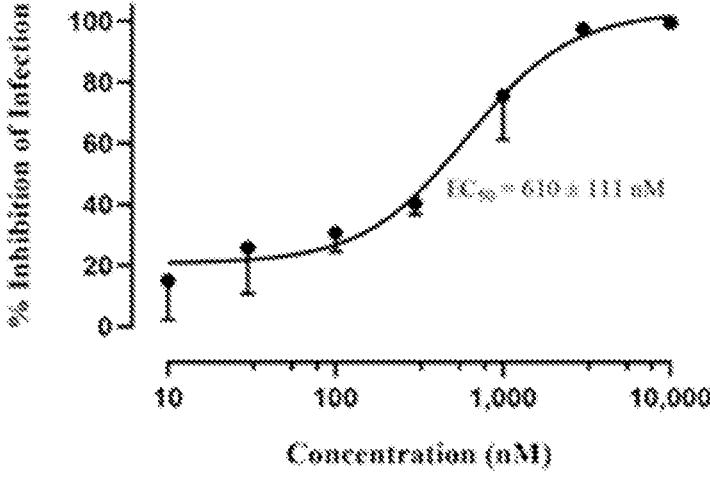
Figure 3C:
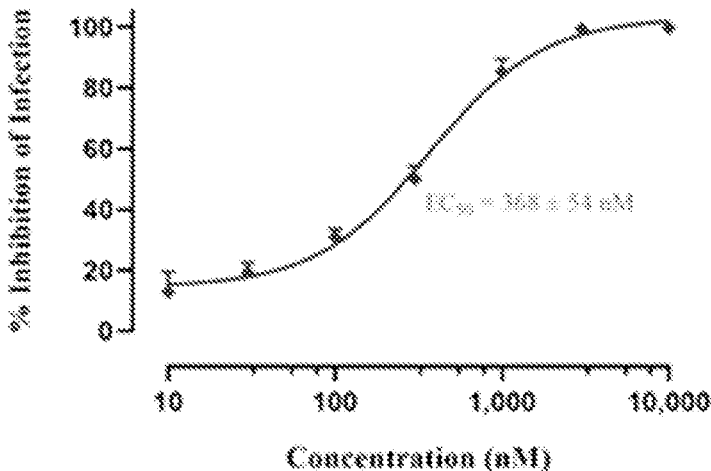

Inhibitory effect of VZMC013 on HIV-1BaL entry into MOR-CCR5 co-expressed TZM-b1 cells. CCR5-expressing TZM-b1 cells co-express an HIV-1 long-terminal repeat (LTR)-firefly luciferase reporter that can be activated by Tat (trans-activator of transcription) in cells expressing HIV. Therefore, increases or decreases in pro-viral gene expression coincide with increases or decreases, respectively, in luciferase activity. To initially determine whether the co-expression of MOR affected HIV-1 entry/expression, OPRM1- or control plasmid-transfected TZM-b1 cells were exposed to varying concentrations of HIV-1BaL and HIV-1 entry was calculated based on LTR-driven luciferase activity. As seen in FIG. 3A, viral entry in TZM-b1 cells expressing MOR was enhanced compared to non-MOR-expressing TZM-b1 cells upon exposure to identical amounts of virus. Our findings indicate that MOR co-expression by itself can be sufficient to enhance the infectivity of R5-tropic HIV in CCR5-expressing cells, which could possibly result from putative MOR-CCR5 heterodimer in addition to the CCR5 mediating the virus entry into host cells. Next, the inhibitory effect of HIV-1BaL infection of the bivalent compound VZMC013 in OPRM1 and control plasmid transfected TZM-b1 cells was measured and compared. VZMC013 demonstrated submicromolar potency in inhibiting HIV-1BaL entry and integration under both circumstances (FIGS. 3B and 3C). More importantly, VZMC013 showed nearly two-fold higher inhibitory potency of virus infection in TZM-b1 cells containing OPRM1 ($EC_{50}$=368 nM) than that of those cells containing only control plasmid ($EC_{50}$=610 nM). The results further suggested that the CCR5 may heterodimerize with the MOR, and the putative MOR-CCR5 complex may play an essential role in facilitating viral entry. In turn, our bivalent ligand VZMC013 may efficiently bind to the putative MOR-CCR5 heterodimers expressed in TZM-b1 cells, and more effectively block HIV entry.

Figure 3D:
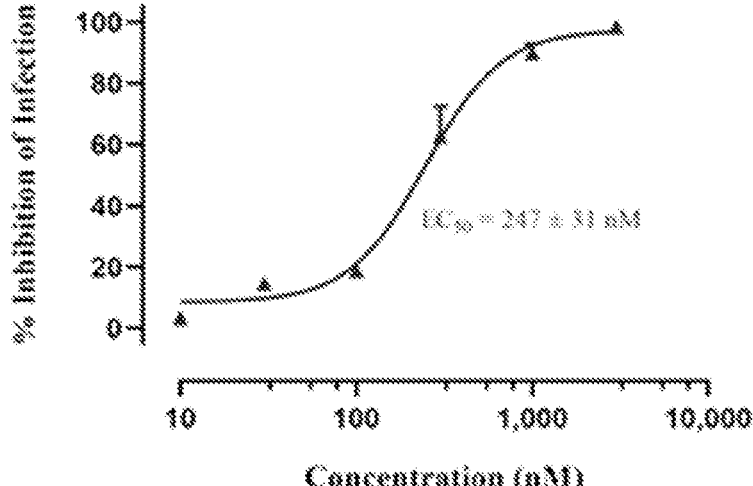

Furthermore, when morphine (100 µM) was added (FIG. 3D), the ability of VZMC013 to inhibit HIV infectivity was enhanced in TZM-b1 cells containing OPRM1 ($EC_{50}$=247 nM) compared to OPRM1-expressing TZM-b1 cells without morphine ($EC_{50}$=368 nM). Therefore, this finding indicates that morphine can exacerbate HIV-1 entry in an MOR-dependent manner and that our bivalent ligand VZMC013 is more potent at suppressing viral entry in the presence of morphine. This further supported our hypothesis that functional MOR-CCR5 dimers may be inhibited effectively by a properly designed bivalent ligand.

Figure 4A:
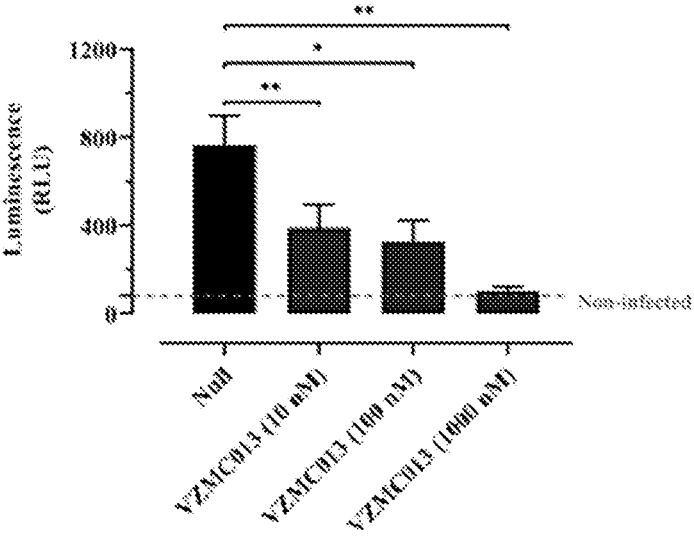
FIGS. 4A and B. A, varying concentrations of VZMC013 were added before PBMC cells were infected by HIV-1BaL Env-pseudotyped Luc-expressing virus (HIV-1-Luc, 1.5 ng p24/well). Luciferase content was expressed as RLU. Null: PBMC cells were infected by HIV-1-Luc, with no ligand added. B, PHA-stimulated PBMCs were exposed to opioids 3 days prior to infection with HIV-1BaL Env-pseudotyped Luc-expressing virus. Morphine (Morph) and DAMGO were used at a concentration of 10 nM. Bivalent compound VZMC013 (100 nM) was added 1 h before the cultures were infected with HIV and maintained in vitro. RLU values of each treatment group were normalized based on the null group (RLU values of the null group were defined as "1"). Null: PHA-stimulated PBMC cells were infected by HIV-1-Luc, with no ligand added. Statistical analysis was performed using GraphPad Prism version 8.0.1 for Windows. Data were analyzed according to one-way ANOVA followed by Newman-Keuls post-hoc test. *$p < 0.05$ and **$p < 0.01$ are considered as statistically significant, and ns: not significant.

Inhibitory effect of VZMC013 on HIV-1 entry to PBMC cells. Peripheral blood mononuclear cells (PBMCs) include large numbers of CCR5-expressing leukocytes and are susceptible to infection by R5-tropic HIV-1 strains. To determine whether VZMC013 would alter HIV infectivity in non-stimulated PBMCs, we used an HTV-1BaL Env-pseudotyped virus encoding a recombinant firefly luciferase gene (HIV-1-Luc). VZMC013 inhibited HIV-1-Luc infectivity in a concentration-dependent manner in PBMCs with a nearly complete blockade at a concentration of 1000 nM (FIG. 4A). These results were as expected since VZMC013 has shown potent CCR5 antagonism profiles in the radioligand binding and calcium mobilization assays.

Figure 4B:
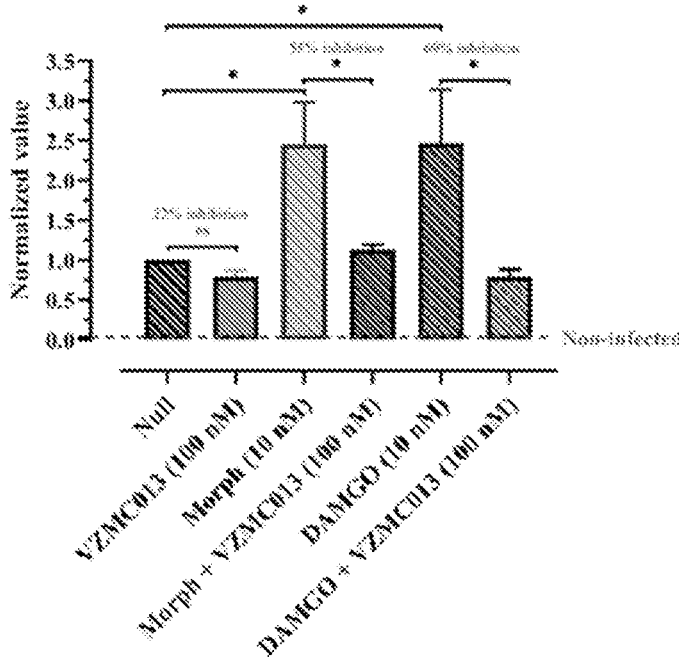

Inhibitory effect of VZMC013 on HIV-1 entry into PHA-stimulated PBMCs. Phytohemagglutinin (PHA) can stimulate PBMCs into cell cycle, and PHA-stimulated PBMCs have been widely utilized for investigating replication of HIV primary isolates in vitro.63 The ability of VZMC013 to inhibit HIV-1 entry into PHA-stimulated PBMCs was further tested. As seen in FIG. 4B, exposure to VZMC013 (100 nM) inhibited viral entry, with a 22% reduction in luminescence.

While exposure to morphine (10 nM) or DAMGO (10 nM) led to remarkable increases in HIV expression in PHA-stimulated PBMCs, VZMC013 (100 nM) was more effective in preventing viral entry, displaying 55% or 69% decreases in HIV expression, respectively, in cells co-exposed to morphine or DAMGO and HIV. These results were in agreement with our findings evaluating HIV-1BaL entry into MOR-CCR5-co-expressing TZM-b1 cells discussed above. That is, MOR agonists may enhance HIV invasion through activation of the MOR-CCR5 dimer while a bivalent ligand specifically inhibiting the heterodimer may effectively block the viral invasion.

Molecular dynamics (MD) simulation studies on VZMC013 with the MOR-CCR5 heterodimer. To delineate the possible binding mode between the bivalent ligand VZMC013 and the putative MOR-CCR5 heterodimer, we implemented molecular modeling studies including molecular docking and molecular dynamics (MD) simulation. Previous studies of the crystal packing interactions of GPCRs revealed that the postulated and observed homodimer interfaces of GPCRs involved TM1/TM2/TM7, TM4/TM5, and TM5/TM6.64 The crystal structure study of the MOR indicated that two different interfaces, TM1/TM2/helix 8 and TM5/TM6, were involved in the dimerization of the MOR and TM5/TM6 is a more prominent interface observed in the ligand-bound MOR crystal structure. The attachment point for the spacer of the bivalent ligands designed, i.e. C6-position of naltrexone, pointed toward the TM5/TM6 in the MOR binding pocket. Based on such observations, TM5/TM6 was selected as the interface of the MOR to dimerize with the CCR5. For the CCR5, previous site-direct mutagenesis studies found that mutations with lysine on TM5 and TM6 did not completely prevent the dimerization of CCR5. Thus, other interfaces may have a higher possibility of being the interface of the CCR5. Moreover, a previous computational study together with the site-direct mutagenesis study revealed that the CCR5 homodimerization involved TM1, TM2, TM3, and TM4. In the present study, considering the fact that the attachment point for the spacer of the bivalent ligands (the 3'-methyl group on the 1,2,4-triazol moiety of maraviroc) pointed toward TM1, TM2, and TM3, and the possible steric hindrance of extracellular loop 1 (ECL1) between TM2 and TM3, TM1/TM2 was therefore selected as the plausible dimer interface of the CCR5.

Figure 5A:
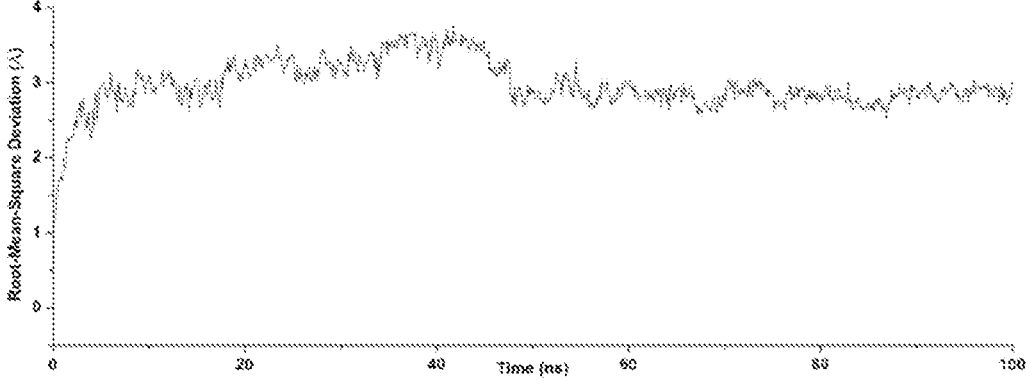
FIGS. 5A and B. The root-mean-square deviation (RMSD, A) and root-mean-square fluctuation (RMSF, B) of the backbone atoms of the proteins in the MOR-CCR5_VZMC013 complex.

A MOR-CCR5 heterodimer model in which TM5/6 of the MOR and TM1/2 of the CCR5 were selected as dimer interfaces in complexing with VZMC013 was inserted into a membrane-aqueous sodium chloride solution system and subjected to further MD simulations. After 100 ns MD simulations, the root-mean-square deviation (RMSD) of the backbone atoms of the proteins was applied to evaluate the dynamic equilibrium of the ligand-receptor complex. As shown in FIG. 5A, for the MOR-CCR5_VZMC013 complex, the average RMSD value for backbone atoms in the protein during the 50-100 ns MD simulation was 2.84 Å. An average RMSD value of less than 3.0 Å for the backbone atoms of the protein has been reported to indicate stable binding. Therefore, the average RMSD value confirmed the thermodynamic equilibrium of the MOR-CCR5_VZMC013 complex after 100 ns MD simulations.

Figure 5B:
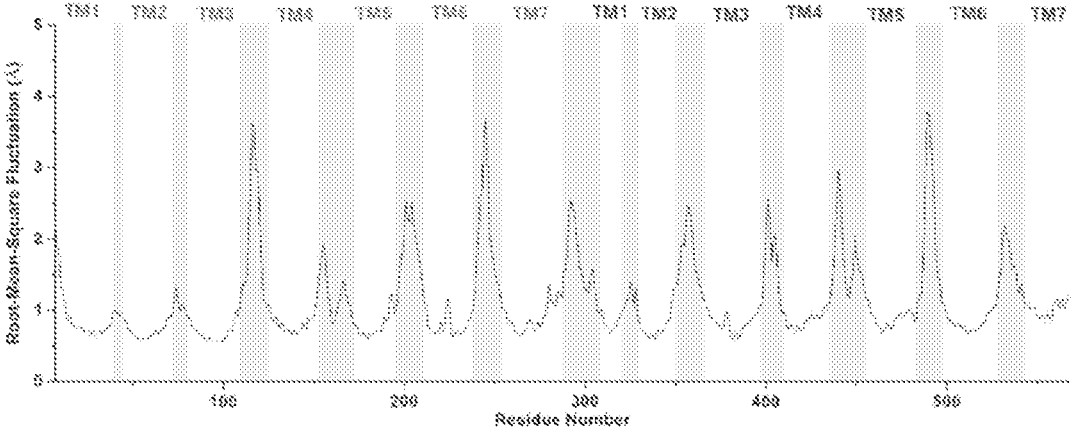

Furthermore, the root-mean-square fluctuation (RMSF) values of the backbone atoms of the protein in the MOR-CCR5_VZMC013 complex were plotted in FIG. 5B. Apparently, residues located in the seven TMs of the MOR-CCR5 dimer displayed more stable conformation than other domains of the two proteins, e.g., intracellular loops (ICLs) and extracellular loops (ECLs). This observation agreed with the fact that the transmembrane spanning domains of GPCRs generally form more rigid and stable conformations than those of ICLs or ECLs. RMSF values obtained from 100 ns MD simulations may further substantiate the stability of the MOR-CCR5_VZMC013 complex. Therefore, the conformations of the MOR-CCR5_VZMC013 complex after 100 ns MD simulations were selected for further analyses.

Figure 6:
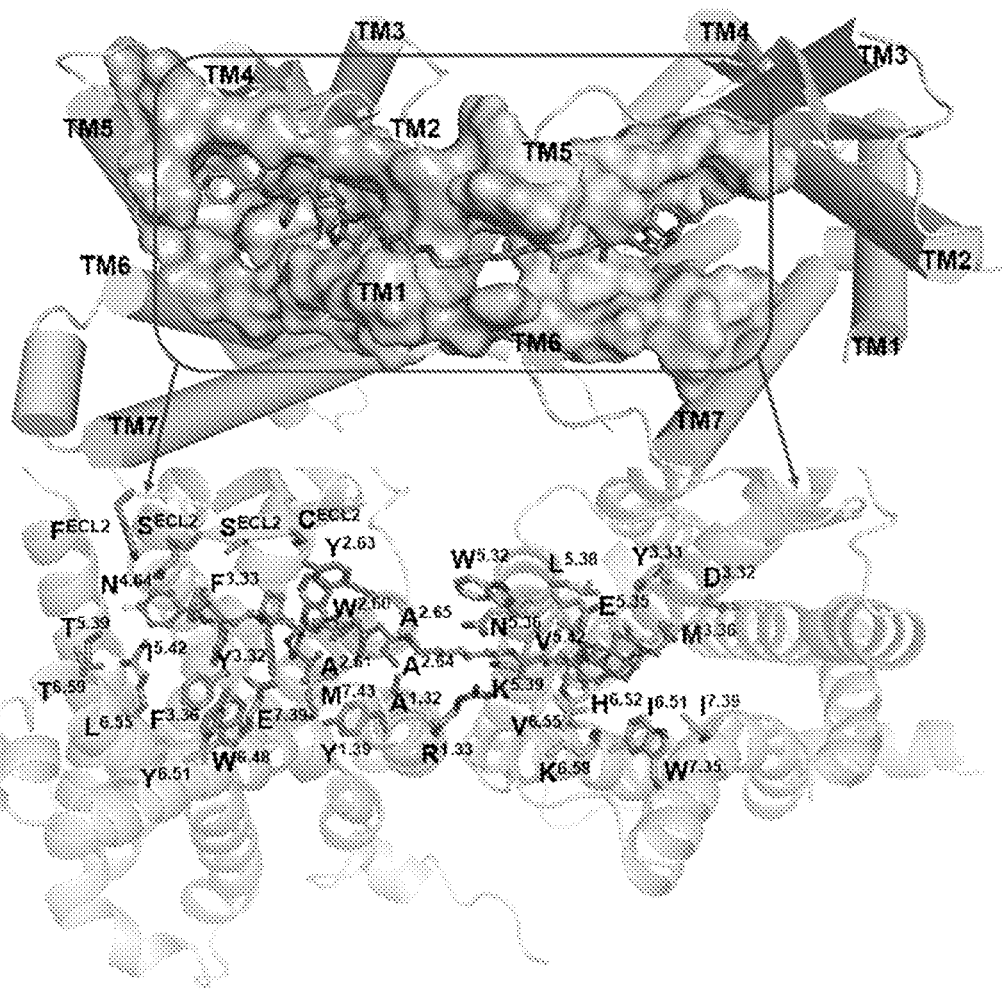
FIG. 6. The binding mode of VZMC013 in the MOR-CCR5 heterodimer complex after MD simulations. The MOR-CCR5 heterodimer (top) is shown as a cylinder model. The MOR-CCR5 heterodimer (bottom) is shown as a cartoon model. The key residues within a 5 Å proximity of VZMC013 are shown as surface models in the top figure and stick models in the bottom figure, respectively. Carbon atom: the key residues directly interacted with the MOR are shown; the key residues directly interacted with the CCR5 are shown. Compound VZMC013 is shown as a stick and ball model.

After MD simulations, the stable binding mode of the MOR-CCR5_VZMC013 complex showed that there were mainly 39 amino acid residues from the two proteins within a 5 Å proximity of the bivalent ligand VZMC013 (FIG. 6). Among them, 19 residues were associated with the CCR5 pharmacophore, 10 of them were in juxtaposition to the MOR pharmacophore, and the remaining 10 to the spacer. As shown in FIG. 6, the CCR5 pharmacophore portion of VZMC013 interacted with amino acid residues from all seven TM helices of CCR5, while the MOR pharmacophore portion of VZMC013 occupied the bottom of a hydrophobic pocket formed mainly by residues from TM3, TM6, and TM7 of the MOR. Residues from TM1-2 of the CCR5 and TM5-6 of the MOR contributed mainly hydrophobic interactions with the spacer.

For comparison purposes, the docking mode of naltrexone, the MOR pharmacophore of VZMC013, in the inactive MOR was depicted first. It seemed that naltrexone may form hydrophobic interactions with residues M1513.36, W2936.48, I2966.51, H2976.52, I3227.39, and Y3267.43. The protonated nitrogen atom at the 17-position of naltrexone formed an ionic interaction with the oxygen atom at the side chain of D1473.32. A hydrogen bonding interaction was formed between the dihydrofuran oxygen atom of naltrexone and the phenolic group of Y1483.33. Similar interactions were also observed in the crystal structure of β-FNA bound to the MOR.46 In the binding of VZMC013 with the MOR-CCR5 heterodimer, the MOR pharmacophore moved closer to TM5 and TM6 of the MOR. This conformational change may somehow weaken the ionic interaction with D1473.32, the hydrogen bonding interaction with Y1483.33, and the hydrophobic interactions with residues W2936.48 and Y3267.43. Distance analyses further supported these observations. On the other hand, residues L2325.38, V2365.42, V3006.55, and W3187.35 seemed to form additional hydrophobic interactions with the MOR pharmacophore, which partially compensated for those weakened interactions. This provided a plausible explanation for the reasonably high binding affinity of VZMC013 to the MOR.

From the crystal structure of maraviroc bound to CCR5, maraviroc binds to the pocket formed by residues from TM1-3 and 5-7 of CCR5. E2837.39 formed an ionic interaction with the protonated nitrogen atom of the tropane moiety. Five hydrogen bonds were formed between maraviroc and the CCR5: two hydrogen bonds between 1'-N, 2'-N of the triazole moiety and residues Y371.39, Y892.63 respectively; one hydrogen bond between the nitrogen atom of the carboxamide group and Y2516.51; and dual hydrogen bonds between one fluorine atom on the cyclohexane ring and residues T1955.39, T2596.59. Moreover, the phenyl group of maraviroc formed hydrophobic interactions with Y1083.32, F1093.33, F1123.36, W2486.48, and Y2516.51. In comparison, an examination of the VZMC013 and MOR-CCR5 heterodimeric binding complex revealed that the spacer induced a rotation of the triazole moiety (the dihedral angle changed from 177.7° to 102.0°). Due to this rotation, the two hydrogen bonding interactions between the triazole moiety of the CCR5 pharmacophore and residues Y371.39 and Y892.63 of CCR5 seemed no longer possible. Moreover, the CCR5 pharmacophore moved closer to the TM1 and TM2 of the CCR5, which may slightly move the CCR5 pharmacophore away from its original binding position thereby decreasing the hydrophobic interactions between the phenyl group of maraviroc and residues Y1083.32, F1093.33, F1123.36, W2486.48, and Y2516.51. Therefore, the relatively lower binding affinity of VZMC013 than maraviroc to the CCR5 seemed reasonable.

On the other hand, the putative movement of the CCR5 pharmacophore towards TM1 and TM2 of the CCR5 may result in amino acid residues C178ECL2, S179ECL2, S180ECL2, F182ECL2 from ECL2 to form stronger interactions with the CCR5 pharmacophore whereas those interactions seemed less obvious in the crystal structure of maraviroc binding to CCR5. Among these, residues C178ECL2 and F182ECL2 formed hydrophobic interactions, and residues S179ECL2 and S180ECL2 formed polar interactions with the CCR5 pharmacophore. These interactions were also supported by distance analyses. In previous studies, it has been demonstrated that the interaction between the ECL2 of CCR5 and the V3 loop of HIV gp120 was critical to the process of HIV accessing the host cell membrane. Particularly, residues R11 and S13 of the V3 loop were involved in polar interactions with residues S179ECL2 and S180ECL2 from the ECL2 of CCR5 (Figure S8, which showed the putative binding between V3 loop of HIV gp120 and CCR5). Therefore, the CCR5 pharmacophore interacted with the ECL2 of CCR5 which may effectively inhibit the V3 loop of gp120 binding to the ECL2 of CCR5 and further block the attachment of HIV to the host cell.

CONCLUSIONS

Utilizing the available ligand-bound crystal structures of the MOR and CCR5, we successfully designed and developed a new bivalent ligand VZMC013 targeting MOR-CCR5 heterodimers. VZMC013 demonstrated prominent binding affinities for both MOR and CCR5 at nanomolar levels, which were much higher affinities than those of the previously reported bivalent ligand VZMC001. [$^{35}$S]GTPγS and calcium mobilization assays of MOR function confirmed VZMC013 to be a potent MOR antagonist as designed. In addition, VZMC013 acted as a CCR5 antagonist and inhibited CCL5-stimulated Ca2+ transients in HOS-CCR5 cells more potently than VZMC001, and this finding was further supported by its significantly improved anti-HIV-1BaL activity at the CCR5 HIV co-receptor. Moreover, VZMC013 showed more potent inhibitory activity of viral infection in TZM-b1 cells co-expressing CCR5 and MOR than in TZM-b1 cells expressing CCR5 alone, implying that the presence of MOR and putative MOR-CCR5 heterodimeric complexes enhance HIV entry, and suggesting that MOR complexation with CCR5 fundamentally alters the functional properties of CCR5 as an HIV co-receptor. Most importantly, VZMC013 was able to block opioid-accelerated HIV-1 invasion more effectively in TZM-b1 cells and PHA-stimulated PBMC cells than in controls (lacking opioids), further suggesting its promising role in inhibiting opioid exacerbated HIV-1 infectivity. Utilizing molecular docking and molecular dynamics simulation approaches, a possible binding mode of VZMC013 in the newly constructed MOR-CCR5 heterodimer model was postulated and helped explain the underlying mechanism of inhibition of viral infection by VZMC013.

In summary, VZMC013 is a potent chemical probe that can be used to investigate the specific functional role of putative MOR-CCR5 heterodimers in viral entry and may also serve as a pharmacological agent to alleviate opioid-dependent increases in HIV entry.

EXPERIMENTAL SECTION

Chemistry. All reagents were purchased from commercial suppliers and with no further purification when used. TLC analyses were performed on the Analtech UNIPLATE™ F254 plates. Spots were visualized by irradiation with UV light (λ254 nm) and iodine vapor. Flash column chromatography was carried out on columns packed with silica gel (230-400 mesh, Merck). 1H NMR (400 MHz), and $^{13}$C NMR (100 MHz) spectra were obtained at ambient temperature with tetramethylsilane (TMS) as the internal standard on a Bruker Ultrashield 400 Plus spectrometer (Bruker, Germany). 19F NMR (376 MHz) spectra were not externally calibrated and chemical shifts are given as received from the automatic data processing with MestReNova.

Chemical shifts were expressed in (units (ppm), and J values were reported in hertz (Hz). HRMS spectra were acquired from a PERKINELMER® Flexar UHPLC with AxION 2 Time of Flight (TOF) Mass Spectrometer (PERKINELMER®, USA). Analysis of the sample purity was performed on a Varian Prostar 210 HPLC (high performance liquid chromatography) system using a column Agilent MICROSORB-MV™ 100-5 C18 column (250×4.6 mm). HPLC eluent conditions: acetonitrile/water (with 0.1% trifluoroacetic acid), fixed at 40%/60%, or acetonitrile increased from 40% to 100% in gradient within 20 min of test. Flow rate, 0.5 mL/min; UV detection, 210 nm; temperature, ambient; injection volume, 5 µL. The purity of all final compounds was identified as >95%.

Preparation of Compound 9

3-amino-3-phenylpropanoic acid (4). To a mixture of malonic acid (1.56 g, 15 mmol) and ammonium formate (1.58 g, 25 mmol) was added a solution of benzaldehyde 3 (1.06 g, 10 mmol) in 30 mL of ethanol. The resulting mixture was refluxed for 5 h, then was cooled to ambient temperature. The mixture was stirred overnight and filtered. The precipitate was washed with cool ethanol to give 4 as a white solid (0.97 g, 59%). 1H NMR (400 MHz, D$_2$O): δ 7.52-7.44 (m, 5H), 4.66-4.63 (m, 1H), 2.94-2.79 (m, 2H). C$_9$H$_{11}$NO$_2$ (165.0790).

Methyl 3-amino-3-phenylpropanoate (5). To a solution of 3-amino-3-phenylpropanoic acid 4 (7.74 g, 46.8 mmol) in MeOH (45 mL) cooled in ice-water bath was dropwise added 5 mL of concentrated sulfuric acid. The resulting mixture was warmed up to ambient temperature and was stirred for 6.5 h. The excess solvent was removed under reduced pressure, and 100 mL of dichloromethane was added to the residue, then the mixture was cooled to 0° C. The pH of the solution was adjusted to 10 using 2M NaOH.

After separation and further extraction with dichloromethane, the organic layers were combined, washed with water, brine, dried over $Na_2SO_4$ and filtered. The filtrate was concentrated to provide 5 as a yellow oil (8.31 g, 99%). 1H NMR (400 MHz, $CDCl_3$): δ 7.38-7.32 (m, 4H), 7.28-7.24 (m, 1H), 4.42 (t, J=6.4 Hz, 1H), 3.68 (s, 3H), 2.67 (d, J=7.6 Hz, 2H), 1.73 (s, 2H). $C_{10}H_{13}NO_2$ (179.0946).

Methyl (S)-3-amino-3-phenylpropanoate L-(+)-tartaric acid salt (5-L-(+)-tartaric acid) (6). A solution of L-(+)-tartaric acid (5.43 g, 36.2 mmol) in MeOH (42 mL) was heated to 45° C. Then, a solution of methyl 3-amino-3-phenylpropanoate 5 (6.48 g, 36.2 mmol) in MeOH (13 mL) was added. The resulting mixture was cooled to ambient temperature and was stirred overnight. The mixture was filtered, and the precipitate was washed with cool MeOH, recrystallized in MeOH for two times, affording 6 as a white crystalline solid (2.98 g, 25%). [α]D20=−20.84 (c 1.12, CHCl3). $C_{14}H_{19}NO_8$ (329.1111).

(S)-3-(((benzyloxy)carbonyl)amino)-3-phenylpropanoic acid (7). To a solution of methyl (S)-3-amino-3-phenylpropanoate L-(+)-tartaric acid salt 6 (0.33 g, 1.0 mmol) in dichloromethane (1.6 mL) was added sodium carbonate aqueous solution (0.35 g of sodium carbonate dissolved in 1.5 mL of $H_2O$) at 0° C. Benzyl chloroformate (0.21 g, 1.2 mmol) was then dropwise added in 1 min and upon completion of the addition the reaction mixture was warmed up to ambient temperature and was stirred at room temperature for 5 h. The water phase was extracted with dichloromethane (5 mL×3), and the combined organic layers were washed with brine, dried over $Na_2SO_4$, filtered, and concentrated to provide a colorless oil. The oil was dissolved in MeOH (4 mL), and the pH was adjusted to 13 with 2 M NaOH at 0° C. The resulting mixture was stirred at this temperature for 4 h. 5 mL of water was added, and then the solution was acidified to pH 1 with 2M HCl. The mixture was filtered, and the precipitate was washed with water and then was re-dissolved in dichloromethane. The organic layer was dried over $Na_2SO_4$, filtered and concentrated to offer 7 as a white solid (0.24 g, 80%). 1H NMR (400 MHz, DMSO-d6): δ 7.90 (d, J=8.60 Hz, 1H, exchangeable), 7.38-7.28 (m, 10H, Ph-H), 5.00-4.96 (m, 3H), 2.74-2.64 (m, 2H). 1H NMR (400 MHz, $CDCl_3$): δ 7.33-7.25 (m, 10H, Ph-H), 5.71-5.70 (m, 1H, exchangeable), 5.17-5.03 (m, 3H), 2.97-2.84 (m, 2H). $^{13}$C NMR (100 MHz, $CDCl_3$): δ 175.9, 155.7, 140.4, 136.2, 128.8, 128.5, 128.2, 127.8, 126.2, 67.1, 51.4, 40.2. HRMS (ESI) m/z calcd. for $C_{17}H_{16}NO_4$ [M−H]−: 298.1079, found: 298.1081.

Benzyl (S)-(3-hydroxy-1-phenylpropyl)carbamate (8). To a solution of (S)-3-(((benzyloxy)carbonyl)amino)-3-phenyl-propanoic acid 7 (1.87 g, 6.24 mmol) in anhydrous THF (10 mL) was added borane tetrahydrofuran complex solution (1.0 M in THF, 24.9 mmol) under $N_2$ protection at 0° C. The resulting mixture was stirred for additional 1 h at room temperature. 2 mL of acetone and 20 mL of water were added. The excess solvent was removed under reduced pressure and 50 mL of saturated sodium bicarbonate solution was then added. The mixture was extracted with ethyl acetate (30 mL×3). The combined organic extracts were washed with saturated sodium bicarbonate solution (50 mL), followed by 0.1 M HCl (30 mL) and brine (50 mL). After being dried over $Na_2SO_4$ and filtering, the filtrate was concentrated to yield a crude product, which was recrystallized with ethyl acetate and hexane to furnish 8 as a white powder (1.03 g, 58%). 1H NMR (400 MHz, $CDCl_3$): δ 7.36-7.27 (m, 10H, Ph-H), 5.39-5.38 (m, 1H), 5.15-5.03 (m, 2H), 4.96-4.95 (m, 1H), 3.70-3.66 (m, 2H), 2.63 (brs, 1H, OH), 2.12-2.04 (m, 1H), 1.92-1.84 (m, 1H). $^{13}$C NMR (100

MHz, $CDCl_3$): δ 156.6, 141.7, 136.3, 128.8, 128.7, 128.6, 128.2, 127.6, 126.4, 67.0, 59.2, 52.6, 39.1. HRMS (ESI) m/z calcd. for $C_{17}H_{19}NNaO_3$ [M+Na]+: 308.1263, found: 308.1277.

Benzyl (S)-(3-oxo-1-phenylpropyl)carbamate (9). Sulfur trioxide pyridine complex (1.73 g, 10.85 mmol) was added to a solution of benzyl (S)-(3-hydroxy-1-phenylpropyl)car-bamate 8 (0.619 g, 2.17 mmol) and triethylamine (2.196 g, 21.7 mmol) in DMSO/dichloromethane (10 mL/10 mL) at 0° C. The mixture was stirred for 0.5 h. Water (100 mL) was added and the mixture was extracted with ethyl acetate (30 mL×3). The combined organic layers were washed with 0.5 M HCl and brine, dried over $Na_2SO_4$, filtered, and concentrated. Further purification of the residue by column chromatography led to 9 as a yellowish solid (0.53 g, 87%). 1H NMR (400 MHz, $CDCl_3$): δ 9.72 (s, 1H, CHO), 7.35-7.27 (m, 10H, Ph-H), 5.45-5.43 (m, 1H, NH), 5.26-5.24 (m, 1H), 5.12-5.00 (m, 2H), 3.03-2.88 (m, 2H). $^{13}$C NMR (100 MHz, $CDCl_3$): δ 199.9, 155.6, 140.6, 136.2, 128.9, 128.5, 128.2, 128.1, 127.9, 126.3, 67.0, 50.6, 49.5. IR (Diamond, cm-1): 3317.00, 3031.58, 2922.38, 1693.15, 1585.06, 1525.06, 1496.85, 1454.47, 1405.38, 1338.29, 1242.68, 1049.96, 1027.24, 913.83, 738.70. HRMS (ESI) m/z calcd. for $C_{17}H_{17}NNaO_3$ [M+Na]+: 306.1106, found: 306.1105; calcd. for $C_{18}H_{21}NNaO_4$ [M+MeOH+Na]+: 338.1368, found: 338.1395. Preparation of compound 13.

Methyl 3-aminopropanoate hydrochloride (11). Thionyl chloride (10.12 g, 75 mmol) was slowly added to methanol (25 mL) at 0° C. The resulting mixture was stirred for 20 min. After the addition of 3-aminopropanoate 10 (2.67 g, 30 mmol), the mixture was stirred at room temperature for 14 h. The solvent was evaporated to give a crude salt, which was further recrystallized using methanol/ether to afford 11 as a white solid (2.60 g, 62%). $C_4H_{10}ClNO_2$ (139.0400).

Methyl 3-((((9H-fluoren-9-yl)methoxy)carbonyl)amino) propanoate (12). Methyl 3-aminopropanoate hydrochloride 11 (0.56 g, 4 mmol) was placed in 10 mL of dichloromethane and the mixture was cooled in an ice-water bath. Triethylamine (1.50 g, 15 mmol) and a solution of Fmoc-Cl (1.09 g, 4.2 mmol) in dichloromethane (10 mL) were added in sequence. The resulting mixture was stirred at ambient temperature for 1.5 h, then the mixture was treated with 0.5 N HCl. The organic layer was washed with saturated sodium bicarbonate solution (30 mL), brine (30 mL), dried over $Na_2SO_4$, filtered, and concentrated. The crude product was purified by column chromatography to supply 12 as a white solid (1.05 g, 81%). 1H NMR (400 MHz, $CDCl_3$): δ 7.77 (d, J=7.52 Hz, 2H, fluorene-H), 7.59 (d, J=7.40 Hz, 2H, fluo-rene-H), 7.40 (t, J=7.40 Hz, 2H, fluorene-H), 7.32 (td, J1=7.44 Hz, J2=0.72 Hz, 2H, fluorene-H), 5.30 (brs, 1H, NH), 4.39 (d, J=6.96 Hz, 2H, OCH2), 4.21 (t, J=6.92 Hz, 1H, CH), 3.71 (s, 3H, OCH₃), 3.48 (q, J=6.00, 2H, CH₂), 2.57 (t, J=5.84, 2H, COCH2). $^{13}$C NMR (100 MHz, $CDCl_3$): δ 172.9, 156.3, 143.9, 141.3, 127.7, 127.1, 125.1, 120.0, 66.8, 51.8, 47.3, 36.6, 34.2. $C_{19}H_{19}NO_4$ (325.1314).

(9H-fluoren-9-yl)methyl (3-hydrazinyl-3-oxopropyl)car-bamate (13). The intermediate 12 (0.32 g, 1.0 mmol) was suspended in methanol (2.5 mL). A solution of hydrazine monohydrate (0.25 g, 5 mmol) in methanol (2.5 mL) was added and the mixture was stirred at room temperature for 30 h. The solvent was removed and the residue was reslur-ried in ethyl acetate and filtered to afford 13 as a white solid (0.16 g, 49%). 1H NMR (400 MHz, DMSO-d6): δ 9.01 (s, 1H), 7.89 (d, J=7.48 Hz, 2H), 7.69 (d, J=7.36 Hz, 2H), 7.42 (t, J=7.36 Hz, 2H), 7.37-7.30 (m, 3H), 4.28 (d, J=6.76 Hz, 2H), 4.23-4.19 (m, 1H), 3.22-3.17 (m, 2H), 2.21 (t, J=7.36 Hz, 2H). $^{13}$C NMR (100 MHz, DMSO-d6): δ 169.8, 157.1, 142.5, 139.4, 137.4, 128.9, 127.3, 121.3, 120.0, 109.7, 37.0, 34.2. $C_{18}H_{19}N_3O_3$ (325.1426).

Preparation of the 2'-aminoethyl Maraviroc Precursor 24

8-Benzyl-8-azabicyclo[3.2.1]octan-3-one (15). Tetrahydro-2,5-dimethoxyfuran (1.32 g, 10 mmol) was placed in 10 mL of 0.1 M HCl and the mixture was stirred at room temperature for 6 h. Then benzylamine (1.29 g, 12 mmol) was mixed with 10 mL of water and 1 mL of concentrated hydrochloric acid, which was added to the above mixture at 0° C. The resulting mixture was adjusted to pH 4 using 1M sodium acetate solution. After the introduction of 1,3-acetonedicarboxylic acid 14 (1.46 g, 10 mmol), the resulting mixture was stirred at room temperature overnight before being filtered. The filtrate was washed with ether, followed by being adjusted to pH 10 with 2 NNaOH. The mixture was extracted with ethyl acetate (50 mL×3). The combined organic layers were washed with brine, dried over $Na_2SO_4$, filtered, and concentrated. The residue was further purified by column chromatography to supply 15 as an oil (1.03 g, 48%). 1H NMR (400 MHz, $CDCl_3$): δ 7.43-7.41 (m, 2H), 7.36-7.32 (m, 2H), 7.29-7.25 (m, 1H), 3.75 (s, 2H), 3.51-3.48 (m, 2H), 2.69 (dd, J1=16.08 Hz, J2=4.44 Hz, 2H), 2.23-2.18 (m, 2H), 2.14-2.07 (m, 2H), 1.66-1.60 (m, 2H). $^{13}C$ NMR (100 MHz, $CDCl_3$): δ 210.8, 139.9, 128.9, 127.6, 59.1, 55.7, 48.8, 28.3. $C_{14}H_{17}NO$ (215.1310).

8-Benzyl-8-azabicyclo[3.2.1]octan-3-one oxime (16). Hydroxylamine hydrochloride (1.03 g, 14.9 mmol) and pyridine (1.29 g, 16.3 mmol) were added to a solution of 8-benzyl-8-azabicyclo[3.2.1]octan-3-one 15 (3.20 g, 14.9 mmol) in 60 mL of ethanol. The resulting mixture was heated to reflux overnight and was allowed to cool to room temperature. The mixture was then diluted with saturated sodium carbonate solution. After filtration, the filtrate was evaporated under reduced pressure to remove the excess solvent. The residue was treated with water (100 mL) and extracted with dichloromethane (60 mL×3). The combined organic layers were washed with brine, dried over $Na_2SO_4$, filtered, and concentrated. The residue was recrystallized with ethanol to afford 8-benzyl-8-azabicyclo[3.2.1]octan-3-one oxime 16 as a crystalline solid (1.74 g, 51%). 1H NMR (400 MHz, DMSO-d6): δ 10.31 (s, 1H, OH), 7.40-7.38 (m, 2H), 7.34-7.30 (m, 2H), 7.26-7.22 (m, 1H), 3.61 (s, 2H, NCH2), 3.26-3.22 (m, 2H), 2.85 (d, J=15.16 Hz, 1H), 2.44 (dd, J1=14.40 Hz, J2=3.04 Hz, 1H), 2.06-2.00 (m, 2H), 1.96-1.90 (m, 2H), 1.49-1.45 (m, 1H), 1.36-1.29 (m, 1H). $^{13}C$ NMR (100 MHz, DMSO-d6): δ 153.3, 139.8, 128.3, 128.1, 126.7, 58.0, 57.3, 54.6, 36.9, 31.0, 27.4, 26.5. HRMS (ESI) m/z calcd. for $C_{14}H_{19}N_2O$ [M+H]+: 231.1497, found: 231.1502.

8-Benzyl-8-azabicyclo[3.2.1]octan-3-amine (17). To a stirring solution of 8-benzyl-8-azabicyclo[3.2.1]octan-3-one oxime 16 (0.46 g, 2 mmol) in 8 mL of 1-pentanol was added sodium (0.46 g, 20 mmol) in portions at 120° C. The resulting mixture was stirred at this temperature for 5 h and then was allowed to cool to 0° C. in an ice-water bath. The mixture was acidified to pH=2 with 6 M HCl and then extracted with 6 M HCL. The combined aqueous layers were basified with 5 M NaOH to pH 10. The resulting mixture was extracted with ethyl acetate (20 mL×3). The combined organic layers were washed with brine, dried over $Na_2SO_4$, filtered, and concentrated to provide 17 as an oil (0.31 g, 72%), which was used for the next step without further purification. 1H NMR (400 MHz, DMSO-d6): δ 8.07 (brs, 2H, $NH_2$), 7.36-7.30 (m, 4H), 7.26-7.21 (m, 1H), 3.58 (s, 2H, NCH2), 3.31-3.22 (m, 1H), 3.17 (s, 2H), 1.97-1.94 (m, 2H), 1.73-1.70 (m, 4H), 1.57-1.52 (m, 2H). $^{13}C$ NMR (100 MHz, DMSO-d6): δ 139.8, 128.3, 128.1, 126.7, 57.0, 54.0, 43.0, 34.1, 26.3. HRMS (ESI) m/z calcd. for $C_{14}H_{21}N_2[M+H]$+: 217.1705, found: 217.1710.

N-(8-benzyl-8-azabicyclo[3.2.1]octan-3-yl)isobutyramide (18). To a stirring mixture of 8-benzyl-8-aza-bicyclo[3.2.1]octan-3-amine 17 (0.22 g, 1.0 mmol) in dichloromethane (6 mL) was added sodium carbonate solution (0.30 g, 2.8 mmol, in 6 mL of $H_2O$). A solution of isobutyryl chloride (0.13 g, 1.2 mmol) in dichloromethane (3 mL) was then added dropwise at 0° C. The resulting mixture was warmed up to room temperature and was stirred for 0.5 h. The mixture was adjusted to pH=9 with saturated sodium bicarbonate solution and was extracted with dichloromethane (5 mL×3). The combined organic layers were washed with 1M NaOH (5 mL), brine, dried over $Na_2SO_4$, filtered, and concentrated. The residue was recrystallized with ethyl acetate/hexane to furnish 18 as a white solid (0.14 g, 49%). 1H NMR (400 MHz, $CDCl_3$): δ 7.37-7.36 (m, 2H, Ph-H), 7.33-7.29 (m, 2H, Ph-H), 7.26-7.22 (m, 1H, Ph-H), 5.25 (d, J=6.64 Hz, 1H, NH), 4.20-4.09 (m, 1H), 3.53 (s, 2H, CH2), 3.22 (brs, 2H), 2.27 (hept, J=6.88 Hz, 1H, CH), 2.05-2.02 (m, 2H), 1.83-1.78 (m, 2H), 1.75-1.70 (m, 2H), 1.53-1.47 (m, 2H), 1.12 (d, J=6.88 Hz, 6H, $CH_3$×2). $^{13}C$ NMR (100 MHz, $CDCl_3$): δ 176.4, 140.0, 128.7, 128.3, 127.0, 59.0, 56.5, 41.2, 38.7, 35.9, 26.5, 19.7. HRMS (ESI) m/z calcd. for $C_{18}H_{27}N_2O$ [M+H]+: 287.2123, found: 287.2132.

(9H-fluoren-9-yl)methyl 2-(4-(8-benzyl-8-azabicyclo[3.2.1]octan-3-yl)-5-isopropyl-4H-1,2,4-triazol-3-yl)ethyl)carbamate (19). To a solution of PC15 (0.77 g, 3.7 mmol) in anhydrous dichloromethane (15 mL) was added dropwise a solution of N-(8-benzyl-8-azabicyclo[3.2.1]octan-3-yl)isobutyramide 18 (0.69 g, 2.4 mmol) in 15 mL of anhydrous dichloromethane over 1 h. After being stirred at room temperature for 5 h, the mixture was treated with addition of a solution of (9H-fluoren-9-yl)methyl(3-hydrazinyl-3-oxopropyl)carbamate 13 (0.60 g, 1.85 mmol) in tert-amyl alcohol (15 mL) over 1 h at 0° C. The resulting mixture was stirred at room temperature for 16 h. The mixture was then treated with saturated sodium bicarbonate solution (15 mL) and was extracted with dichloromethane (30 mL×3). The combined organic layers were washed with brine, dried over $Na_2SO_4$ and concentrated to ca. 10 mL. After the addition of acetic acid (1.2 mL), the mixture was heated at 85° C. for 2 h. The reaction was quenched by the addition of saturated sodium bicarbonate solution (50 mL) and was extracted with ethyl acetate (50 mL×3). The combined organic phases were washed with brine, dried over $Na_2SO_4$ and concentrated. The residue was further purified by column chromatography to give 19 as a white crystalline solid (0.31 g, 29%). 1H NMR (400 MHz, DMSO-d6): δ 7.88 (d, J=7.52 Hz, 2H), 7.67 (d, J=7.44 Hz, 2H), 7.55 (t, J=5.68 Hz, 1H, exchangeable), 7.43-7.38 (m, 4H), 7.33-7.27 (m, 4H), 7.20 (t, J=7.24 Hz, 1H), 4.33-4.30 (m, 2H), 4.29-4.20 (m, 2H), 3.55 (brs, 2H), 3.40-3.36 (m, 2H), 3.23-3.17 (m, 3H), 2.96 (t, J=7.48 Hz, 2H), 2.12-2.03 (m, 4H), 1.73-1.68 (m, 4H), 1.28 (d, J=6.76 Hz, 6H). $^{13}C$ NMR (100 MHz, DMSO-d6): δ 158.3, 156.1, 151.0, 143.8, 140.6, 139.8, 128.1, 128.0, 127.5, 126.9, 126.5, 125.0, 120.0, 65.4, 58.3, 55.4, 46.6, 36.5, 26.3, 25.8, 25.0, 21.9. IR (Diamond, cm-1): 3320.83, 2933.60, 2875.13, 2160.60, 1979.45, 1712.86, 1507.73, 1449.25, 1349.55, 1312.41, 1247.11, 1138.87, 1099.09, 1071.14, 1029.43, 969.64, 920.53, 876.36, 844.60, 797.40, 758.76, 738.58, 696.58. $C_{36}H_{41}N_5O_2$ (575.3260). (9H-fluoren-9-yl) methyl 2-(4-(8-azabicyclo[3.2.1]octan-3-yl)-5-isopropyl-4H-1,2,4-triazol-3-yl)ethyl)carbamate (20 tosylate). A solution of compound 19 (0.46 g, 0.80 mmol) in anhydrous methanol (10 mL) was hydrogenated in the presence of 30% Pd—C (0.14 g) and p-toluenesulfonic acid monohydrate (0.15 g, 0.80 mmol) under a hydrogen atmosphere (60 psi) at room temperature for 24 h. The mixture was filtered through celite, and the filtrate was concentrated to afford 20 as a tosylate salt, which was directly used for the next step due to a stability issue of the free amine. HRMS (ESI) m/z calcd. for $C_{29}H_{36}N_5O_2$ [M+H]+: 486.2869, found: 486.2881; calcd. For $C_{29}H_{35}N_5NaO_2$ [M+Na]+: 508.2688, found: 508.2701.

Benzyl((S)-3-(3-(3-(2-((((9H-fluoren-9-yl)methoxy)carbonyl)amino)ethyl)-5-isopropyl-4H-1,2,4-triazol-4-yl)-8-azabicyclo[3.2.1]octan-8-yl)-1-phenylpropyl)carbamate (21). To a mixture of the 20-tosylate salt got from the last step and compound 9 (0.25 g, 0.88 mmol) in dichloromethane (10 mL) were added acetic acid (0.28 mL) and sodium triacetoxyborohydride (0.19 g, 0.88 mmol) in sequence. After being stirred at room temperature overnight, the reaction was quenched by addition of saturated sodium bicarbonate solution and the mixture was extracted with dichloromethane (30 mL×3). The combined organic layers were washed with brine, dried over $Na_2SO_4$, and concentrated. The residue was purified by column chromatography to supply 21 as a white solid (0.32 g, two-step yield: 53%). 1H NMR (400 MHz, DMSO-d6): δ 7.88 (d, J=7.48 Hz, 2H), 7.86-7.81 (m, 1H), 7.65 (d, J=7.36 Hz, 2H), 7.46-7.39 (m, 3H), 7.32-7.19 (m, 12H), 5.06-4.94 (m, 2H), 4.80-4.74 (m, 1H), 4.30 (d, J=6.96 Hz, 2H), 4.23-4.17 (m, 1H), 3.42-3.35 (m, 2H), 3.30-3.28 (m, 1H), 3.25-3.22 (m, 2H), 3.20-3.17 (m, 1H), 2.88 (t, J=7.12 Hz, 2H), 2.34-2.89 (m, 2H), 2.05-1.99 (m, 2H), 1.92-1.75 (m, 4H), 1.67-1.65 (m, 4H), 1.27-1.25 (m, 6H). $^{13}$C NMR (100 MHz, DMSO-d6): δ 158.5, 156.1, 155.5, 150.9, 143.84, 143.83, 140.7, 128.25, 128.20, 128.15, 127.7, 127.61, 127.55, 127.0, 126.6, 126.3, 125.1, 120.1, 79.3, 78.9, 78.6, 66.4, 65.4, 65.1, 58.7, 58.3, 53.0, 46.8, 46.7, 36.5, 25.2, 22.0. HRMS (ESI) m/z calcd. for $C_{46}H_{53}N_6O_4$ [M+H]+: 753.4128, found: 753.4135; calcd. for $C_{46}H_{52}N_6NaO_4$ [M+Na]+: 775.3948, found: 775.3945.

(9H-fluoren-9-yl)methyl(2-(4-(8-((S)-3-amino-3-phenylpropyl)-8-azabicyclo[3.2.1]octan-3-yl)-5-isopropyl-4H-1,2,4-triazol-3-yl)ethyl)carbamate (22). To a solution of compound 21 (0.10 g, 0.13 mmol) in anhydrous methanol (8 mL) was added 30% Pd/C (0.03 g). The mixture was hydrogenated under a hydrogen atmosphere (60 psi) at room temperature for 20 h. The mixture was filtered through celite and washed with methanol. The combined filtrate was concentrated under reduced pressure to provide 22 as a white solid (55 mg, 67%). Compound 22 could be used for next-step reaction without any further purification. 1H NMR (400 MHz, DMSO-d6): δ 7.90-7.84 (m, 3H), 7.59 (d, J=7.36 Hz, 1H), 7.44-7.26 (m, 8H), 7.20 (t, J=7.36 Hz, 1H), 6.29 (s, 1H), 4.31-4.13 (m, 1H), 3.95 (q, J=7.52 Hz, 1H), 3.14-3.06 (m, 2H), 2.97-2.81 (m, 3H), 2.47-2.46 (m, 1H), 2.38-2.29 (m, 2H), 2.13-2.00 (m, 2H), 1.94-1.89 (m, 2H), 1.83 (brs, 2H), 1.76-1.64 (m, 6H), 1.47 (d, J=7.40 Hz, 1H), 1.26 (d, J=6.72 Hz, 6H). HRMS (ESI) m/z calcd. for $C_{38}H_{47}N_6O_2$ [M+H]+: 619.3760, found: 619.3725.

(9H-fluoren-9-yl)methyl (2-(4-(8-((S)-3-(4,4-difluorocyclohexane-1-carboxamido)-3-phenylpropyl)-8-azabicyclo[3.2.1]octan-3-yl)-5-isopropyl-4H-1,2,4-triazol-3-yl)ethyl)carbamate (23). A mixture of 4,4-difluorocyclohexanecarboxylic acid (27 mg, 0.16 mmol), EDCI (31 mg, 0.16 mmol), HOBt (22 mg, 0.16 mmol), trimethylamine (33 mg, 0.32 mmol) and 4 Å molecular sieves in anhydrous dichloromethane (3 mL) was stirred at 0° C. for 0.5 h. Then, compound 22 (50 mg, 0.08 mmol) in dichloromethane (1 mL) was slowly added to the mixture. The reaction temperature was warmed to room temperature and was stirred overnight. The mixture was filtered and the filtrate was concentrated under reduced pressure to get crude residue. The residue was further purified by column chromatography to get compound 23 as a white foam solid (33 mg, 54%). 1H NMR (400 MHz, CD$_3$OD): δ 7.68 (d, J=7.60 Hz, 2H), 7.49 (d, J=7.48 Hz, 2H), 7.29-7.11 (m, 9H), 4.97 (t, J=7.48 Hz, 1H), 4.79 (d, J=3.08 Hz, 1H), 4.36-4.27 (m, 1H), 4.19 (d, J=6.96 Hz, 1H), 4.05 (t, J=6.84 Hz, 1H), 3.54-3.53 (m, 1H), 3.41-3.37 (m, 1H), 3.26-3.23 (m, 2H), 2.95 (t, J=7.04 Hz, 2H), 2.36-2.31 (m, 1H), 2.29-2.19 (m, 1H), 2.15-2.07 (m, 2H), 2.00-1.83 (m, 6H), 1.75-1.59 (m, 9H), 1.25 (d, J=6.84 Hz, 6H), 1.19 (s, 2H), 0.82-0.75 (m, 1H). $^{13}$C NMR (100 MHz, CD$_3$OD): δ 176.7, 145.3, 144.0, 142.6, 129.7, 128.8, 128.3, 128.2, 127.73, 127.66, 126.2, 121.0, 78.3, 71.6, 67.9, 61.1, 60.8, 60.4, 56.3, 52.7, 52.6, 44.3, 43.7, 43.6, 40.5, 40.4, 38.4, 37.7, 37.6, 37.54, 37.48, 36.4, 36.3, 36.2, 34.14, 34.09, 34.07, 33.90, 33.89, 33.86, 33.85, 33.81, 33.7, 33.61, 33.58, 27.3, 27.2, 27.04, 26.98, 26.9, 26.8, 22.3, 22.23, 22.20. 19F NMR (376 MHz, CD$_3$OD): δ −103.31, −102.67, −93.67, −93.04. HRMS (ESI) m/z calcd. for $C_{45}H_{55}F_2N_6O_3$[M+H]+: 765.4304, found: 765.4280; calcd. for $C_{45}H_{54}F_2N_6NaO_3$ [M+Na]+: 787.4123, found: 787.4097.

N—((S)-3-(3-(3-(2-aminoethyl)-5-isopropyl-4H-1,2,4-triazol-4-yl)-8-azabicyclo[3.2.1]octan-8-yl)-1-phenylpropyl)-4,4-difluorocyclohexane-1-carboxamide (24). A mixture of compound 23 (0.10 g, 0.13 mmol) in 20% piperidine/DMF (4 mL) was stirred at room temperature for 1 h. The mixture was then concentrated under reduced pressure to get a crude residue. The residue was further purified by column chromatography to afford 24 as a white solid (30 mg, 42%). 1H NMR (400 MHz, CDCl$_3$): δ 7.38-7.34 (m, 2H), 7.29-7.27 (m, 3H), 6.38 (d, J=7.36 Hz, 1H), 5.16 (q, J=7.32 Hz, 1H), 4.35-4.26 (m, 1H), 3.49 (s, 1H), 3.40-3.35 (m, 2H), 3.23 (t, J=6.24 Hz, 2H), 3.05-2.93 (m, 3H), 2.43 (t, J=6.72 Hz, 2H), 2.29-2.12 (m, 5H), 2.07-1.93 (m, 4H), 1.90-1.77 (m, 6H), 1.66-1.61 (m, 4H), 1.39 (dd, J1=6.80 Hz, J2=1.20 Hz, 6H), 1.26 (s, 1H). $^{13}$C NMR (100 MHz, CDCl$_3$): (173.2, 159.1, 141.9, 128.9, 127.6, 126.5, 77.2, 59.1, 58.3, 52.0, 50.9, 48.0, 47.2, 42.9, 39.9, 36.0, 35.8, 34.9, 33.08, 33.05, 32.9, 32.83, 32.81, 32.79, 32.60, 32.56, 30.5, 26.8, 26.7, 26.1, 26.0, 25.9, 21.8, 1.0. 19F NMR (376 MHz, CDCl$_3$): δ −92.83, −93.46, −100.30, −100.93. HRMS (ESI) m/z calcd. for $C_{30}H_{45}F_2N_6O$ [M+H]+: 543.3623, found: 543.3630; calcd. for $C_{30}H_{44}F_2N_6NaO$ [M+Na]+: 565.3442, found: 565.3438.

Preparation of the Bivalent Ligands VZMC013, VZMC017 and VZMC019

Benzyl-(7-aminoheptyl)carbamate (26a). To a stirring solution of 1,7-diaminoheptane 25a (0.90 g, 6.91 mmol) in MeOH (80 mL) at 0° C. was dropwise added the solution of benzyl chloroformate (1.18 g, 6.91 mmol) in dichloromethane (80 mL) within 5 h while keeping the temperature at 0° C. The reaction mixture was stirred at room temperature overnight, and then the excess solvent was removed under reduced pressure. Dichloromethane (100 mL) and water (100 mL) were added, and the mixture was adjusted to pH 2 with 6 N HCl. The layers were separated. The aqueous layer was washed with dichloromethane (50 mL×2), then was adjusted to pH 12 using 10 N NaOH and was extracted with dichloromethane (50 mL×3). The combined organic layers were dried over $Na_2SO_4$, concentrated and recrystallized with methanol to give 26a as a white solid (0.55 g, 30%). 1H NMR (400 MHz, DMSO-d6): δ 7.38-7.28 (m, 5H), 7.20 (brs, 1H, exchangeable), 5.00 (s, 2H), 2.98 (q, J=2.4 Hz, 2H), 2.53-2.51 (m, 2H), 2.04 (brs, 2H, exchangeable), 1.41-1.38 (m, 2H), 1.34-1.31 (m, 2H), 1.24 (s, 6H). $^{13}$C NMR (100 MHz, DMSO-d6): δ 156.0, 137.3, 128.2, 127.6, 127.6, 65.0, 41.4, 33.0, 29.3, 28.6, 26.3, 26.2. $C_{15}H_{24}N_2O_2$ (264.1838).

Benzyl (9-aminononyl)carbamate (26b). This compound was prepared in a similar way as 26a, using 1,9-diaminon-onane as the starting material. White solid. Yield: 49%. 1H NMR (400 MHz, CDCl$_3$): δ 7.36-7.29 (m, 5H, Ph-H), 5.09 (s, 2H, CH2), 4.74 (brs, 1H, exchangeable), 3.18 (q, J=6.76 Hz, 2H), 2.68 (t, J=6.96 Hz, 2H), 1.50-1.40 (m, 5H), 1.28 (brs, 11H). $^{13}$C NMR (100 MHz, CDCl$_3$): δ 157.7, 138.9, 130.0, 129.4, 129.3, 66.7, 42.5, 41.7, 33.7, 31.0, 30.6, 30.5, 30.3, 28.0, 27.8. HRMS (ESI) m/z calcd. for $C_{17}H_{29}N_2O_2$ [M+H]+: 293.2229, found: 293.2228; calcd. for $C_{17}H_{28}N_2NaO_2$ [M+Na]+: 315.2048, found: 315.2038.

Benzyl (5-aminopentyl)carbamate (26c). This compound was prepared in a similar way as 26a, using cadaverine as the starting material. White solid. Yield: 31%. 1H NMR (400 MHz, CDCl$_3$): δ 7.36-7.28 (m, 5H, Ph-H), 5.09 (s, 2H), 4.90 (brs, 1H, exchangeable), 3.19 (q, J=6.44 Hz, 2H), 2.69 (t, J=6.80 Hz, 2H), 2.21 (brs, 2H, exchangeable), 1.55-1.43 (m, 4H), 1.38-1.31 (m, 2H). HRMS (ESI) m/z calcd. for $C_{13}H_{21}N_2O_2$ [M+H]+: 237.1603, found: 237.1609.

3,13-Dioxo-1-phenyl-2,15-dioxa-4,12-diazaheptadecan-17-oic acid (27a). To a stirring solution of benzyl-(7-ami-noheptyl)carbamate 26a (2.76 g, 10.46 mmol) in THF (20 mL) was added diglycolic anhydride (1.27 g, 10.98 mmol) in three portions. The resulting mixture was stirred at room temperature for 21 h. The excess solvent was removed under reduced pressure, and the residue was recrystallized by ethyl acetate/hexane to provide 27a as a white solid (3.10 g, 78%). 1H NMR (400 MHz, DMSO-d6): δ 12.80 (s, 1H, exchange-able), 7.80 (s, 1H, exchangeable), 7.38-7.28 (m, 5H), 7.19 (s, 1H, exchangeable), 5.00 (s, 2H), 4.10 (s, 2H), 3.94 (s, 2H), 3.08 (q, J=6.80 Hz, 2H), 2.98 (q, J=6.80 Hz, 2H), 1.42-1.37 (m, 4H), 1.24 (s, 6H). HRMS (ESI) m/z calcd. for $C_{19}H_{28}N_2NaO_6$ [M+Na]+: 403.1845, found: 403.2027.

3,15-Dioxo-1-phenyl-2,17-dioxa-4,14-diazanonadecan-19-oic acid (27b). This compound was prepared in a similar way as 27a. White solid. Yield: 86%. 1H NMR (400 MHz, DMSO-d6): δ 7.85 (t, J=5.60 Hz, 1H, exchangeable), 7.39-7.29 (m, 5H), 7.22 (t, J=5.52 Hz, 1H, exchangeable), 5.00 (s, 2H), 4.10 (s, 2H), 3.94 (s, 2H), 3.09 (q, J=6.72 Hz, 2H), 2.98 (q, J=6.72 Hz, 2H), 1.42-1.39 (m, 4H), 1.24 (brs, 10H). $^{13}$C NMR (100 MHz, DMSO-d6): δ 171.5, 168.5, 156.0, 137.3, 128.3 (Ph-C×2), 127.7, 127.7 (Ph-C×2), 70.2, 67.9, 65.0, 40.2, 38.1, 29.4, 29.1, 28.9, 28.7 (CH2×2), 26.3, 26.2. HRMS (ESI) m/z calcd. for $C_{21}H_{31}N_2O_6$ [M−H]−: 407.2182, found: 407.2179.

3,11-Dioxo-1-phenyl-2,13-dioxa-4,10-diazapentadecan-15-oic acid (27c). This compound was prepared in a similar way as 27a. White solid. Yield: 70%. 1H NMR (400 MHz, DMSO-d6): δ 7.87 (t, J=5.28 Hz, 1H, exchangeable), 7.39-7.29 (m, 5H), 7.22 (t, J=5.52 Hz, 1H, exchangeable), 5.01 (s, 2H), 4.10 (s, 2H), 3.94 (s, 2H), 3.08 (q, J=6.72 Hz, 2H), 2.98 (q, J=6.72 Hz, 2H), 1.45-1.37 (m, 4H), 1.27-1.20 (m, 2H). HRMS (ESI) m/z calcd. for $C_{17}H_{23}N_2O_6$ [M−H]−: 351.1556, found: 351.1551.

17-Cyclopropylmethyl-3,14p-dihydroxy-4,5α-epoxy-6p-(3',13'-dioxo-1'-phenyl-2',15'-dioxa-4',12'-diazaheptade-canamido)morphinan (28a). The title compound was pre-pared following the general amide coupling procedure by reacting acid 27a with 60-naltrexamine hydrochloride (prepared according to the method reported by our Group 61) in DMF overnight. The crude product was further purified by column chromatography to furnish 28a as a white solid. Yield: 36%. 1H NMR (400 MHz, CDCl$_3$): δ 7.48 (s, 1H), 7.30-7.35 (m, 5H), 6.82 (s, 1H), 6.73 (d, J=8.04 Hz, 1H), 6.56 (d, J=8.08 Hz, 1H), 5.30 (s, 1H), 5.09 (s, 2H), 4.84 (s, 1H), 4.43 (s, 1H), 4.06-4.05 (m, 5H), 3.35-3.27 (m, 2H), 3.21-3.16 (m, 2H), 3.11-3.06 (m, 1H), 3.01 (s, 1H), 2.66 (m, 2H), 2.37 (m, 2H), 2.21 (m, 2H), 1.68-1.63 (m, 3H), 1.53-1.48 (m, 7H), 1.33 (s, 7H), 0.82 (m, 1H), 0.55-0.54 (m, 2H), 0.15-0.14 (m, 2H). $^{13}$C NMR (100 MHz, CDCl$_3$): δ 168.4, 168.2, 156.0, 142.1, 140.4, 137.3, 128.3, 127.7, 127.6, 118.4, 117.1, 90.5, 70.4, 70.4, 69.6, 65.0, 61.8, 58.4, 50.6, 47.0, 38.2, 30.3, 30.0, 29.3, 29.2, 28.4, 26.4, 26.2, 24.5, 22.2, 9.2, 3.7, 3.5. HRMS (ESI) m/z calcd. for $C_{39}H_{53}N_4O_8$ [M+H]+: 705.3863, found: 705.3982.

17-Cyclopropylmethyl-3,14p-dihydroxy-4,5α-epoxy-6p-(3',15'-dioxo-1'-phenyl-2',17'-dioxa-4',14'-diazanonade-canamido)morphinan (28b). This compound was prepared in a similar way as 28a, by coupling acid 27b with 60-naltr-examine hydrochloride. White solid. Yield: 61%. 1H NMR (400 MHz, CD$_3$OD): δ 7.34-7.27 (m, 5H), 6.63 (d, J=8.12 Hz, 1H), 6.57 (d, J=8.16 Hz, 1H), 5.06 (s, 2H), 4.53 (d, J=7.60 Hz, 1H), 4.06 (s, 2H), 4.05 (s, 2H), 3.80-3.74 (m, 1H), 3.26 (t, J=7.20 Hz, 2H), 3.14-3.06 (m, 4H), 2.70-2.61 (m, 2H), 2.46-2.36 (m, 2H), 2.29-2.22 (m, 1H), 2.18-2.12 (m, 1H), 1.95-1.86 (m, 1H), 1.61-1.43 (m, 8H), 1.32 (brs, 10H), 0.93-0.84 (m, 1H), 0.58-0.49 (m, 2H), 0.20-0.12 (m, 2H). $^{13}$C NMR (100 MHz, CD$_3$OD): δ 171.5, 171.4, 158.9, 143.7, 141.9, 138.6, 132.5, 129.5, 128.9, 128.8, 125.4, 120.1, 118.6, 92.9, 71.7, 71.6, 71.5, 67.3, 63.7, 60.3, 52.5, 48.9, 45.3, 41.8, 40.1, 31.9, 31.2, 30.9, 30.6, 30.5, 30.4, 28.0, 27.8, 25.5, 23.5, 10.3, 4.5, 4.2. HRMS (ESI) m/z calcd. for $C_{41}H_{57}N_4O_8$ [M+H]+: 733.4176, found: 733.4187; calcd. for $C_{41}H_{56}N_4NaO_8$ [M+Na]+: 755.3996, found: 755.3992.

17-Cyclopropylmethyl-3,14p-dihydroxy-4,5α-epoxy-6p-(3',11'-dioxo-1'-phenyl-2',13'-dioxa-4',10'-diazapentade-canamido)morphinan (28c). This compound was prepared in a similar way as 28a, by coupling acid 27c with 60-naltr-examine hydrochloride. White solid. Yield: 60%. 1H NMR (400 MHz, CD$_3$OD): δ 7.37-7.27 (m, 5H), 6.65 (d, J=8.12 Hz, 1H), 6.59 (d, J=8.16 Hz, 1H), 5.09 (s, 2H), 4.57 (d, J=7.56 Hz, 1H), 4.11-4.05 (m, 4H), 3.82-3.76 (m, 1H), 3.32-3.28 (m, 2H), 3.17-3.12 (m, 3H), 2.99 (q, J=7.24 Hz, 1H), 2.76-2.70 (m, 2H), 2.53-2.45 (m, 2H), 2.36-2.23 (m, 2H), 2.00-1.90 (m, 1H), 1.65-1.32 (m, 10H), 0.98-0.89 (m, 1H), 0.61-0.58 (m, 2H), 0.23-0.22 (m, 2H). HRMS (ESI) m/z calcd. for $C_{37}H_{49}N_4O_8$ [M+H]+: 677.3550, found: 677.3562; calcd. for $C_{37}H_{48}N_4NaO_8$ [M+Na]+: 699.3370, found: 699.3369. Compounds 29a-c and 30a-c were pre-pared as previously reported.32, 34

Bivalent Ligand VZMC013

The target compound was prepared following the general amide coupling procedure reported by our group,72 by reacting the 2'-aminoethyl maraviroc precursor 24 with the acid 30a in DMF overnight. The crude product was further purified by column chromatography to afford VZMC013 as a white solid. Yield: 20%. Compound VZMC013 was con-verted to its hydrochloride salt for biological assays. 1H NMR (400 MHz, CDCl$_3$): δ 8.18-8.16 (m, 1H), 7.56-7.52 (m, 1H), 7.34-7.27 (m, 4H), 7.04 (brs, 1H), 6.74-6.71 (m, 1H), 6.54 (d, J=8.16 Hz, 1H), 6.49-6.47 (m, 1H), 5.12-5.07 (m, 1H), 4.43 (d, J=6.08 Hz, 1H), 4.37-4.28 (m, 1H), 4.05 (s, 1H), 4.02 (s, 2H), 3.98 (s, 3H), 3.74-3.64 (m, 3H), 3.40 (brs, 2H), 3.34-3.25 (m, 5H), 3.11-3.09 (m. 1H), 3.04-3.00 (m, 4H), 2.65-2.60 (m, 2H), 2.43-2.37 (m, 4H), 2.25-2.11 (m, 8H), 2.08-2.05 (m, 2H), 2.02-1.97 (m, 2H), 1.92-1.85 (m, 4H), 1.84-1.74 (m, 5H), 1.67-1.65 (m, 6H), 1.62-1.60 (m, 1H), 1.57-1.52 (m, 5H), 1.48-1.44 (m, 2H), 1.38 (d, J=8.84 Hz, 6H), 1.33 (brs, 4H), 1.26 (s, 2H), 0.90-0.79 (m, 2H), 0.54 (d, J=8.12 Hz, 2H), 0.13 (d, J=4.56 Hz, 2H). $^{13}$C NMR (100 MHz, CDCl$_3$): δ 173.6, 169.0, 168.9, 168.8, 168.6, 159.4, 152.8, 143.5, 142.1, 140.0, 131.0, 129.0, 127.7, 126.7, 119.3, 118.2, 92.1, 71.3, 71.2, 71.1, 70.9, 70.2, 62.6, 59.5, 58.9, 51.9, 50.3, 48.7, 47.7, 47.5, 44.21, 44.19, 44.17, 43.0, 39.2, 39.1, 36.5, 33.0, 29.9, 29.4, 29.3, 28.7, 26.7, 26.6, 26.2, 26.15, 26.07, 26.0, 23.7, 22.9, 21.85, 21.83, 9.6, 4.2, 4.1, 4.0. 19F NMR (376 MHz, CDCl$_3$): δ −92.75, −92.38, −100.27, −100.89. IR (Diamond, cm$^{-1}$): 3246.08, 2536.28, 2159.05, 2027.61, 1976.79, 1648.71, 1545.36, 1450.68, 1373.09, 1325.41, 1232.43, 1126.20, 1033.83, 962.12, 936.21, 916.27, 877.82, 856.61, 747.87, 702.53. HRMS (ESI) m/z calcd. for C$_{65}$H$_{93}$F$_2$N$_{10}$O$_{10}$ [M+H]+: 1211.7044, found: 1211.7048; calcd. for C$_{65}$H$_{94}$F$_2$N$_{10}$O$_{10}$ [M+2H]2+: 606.3561, found: 606.3527. HPLC purity: 99.43%. Rt: 6.768 min.

Bivalent Ligand VZMC017

This target compound was prepared in a similar way as VZMC013, by coupling the 2'-aminoethyl maraviroc precursor 24 with 30b. White solid. Yield: 45%. Compound VZMC017 was converted to its hydrochloride salt for biological assays. 1H NMR (400 MHz, CDCl$_3$): δ 8.21-8.15 (m, 1H), 7.57-7.55 (m, 1H), 7.37-7.27 (m, 4H), 7.17-7.12 (m, 1H), 6.94 (brs, 1H), 6.75-6.71 (m, 1H), 6.56-6.53 (m, 1H), 6.44-6.40 (m, 1H), 5.24 (brs, 1H), 5.14-5.07 (m, 2H), 4.41 (dd, J1=5.52 Hz, J2=2.00 Hz, 1H), 4.36-4.27 (m, 1H), 4.07-4.00 (m, 4H), 3.98 (s, 3H), 3.80-3.70 (m, 2H), 3.40 (brs, 2H), 3.36-3.29 (m, 3H), 3.28-3.21 (m, 3H), 3.19-3.15 (m, 2H), 3.11-3.10 (m. 1H), 3.06-2.98 (m, 4H), 2.68-2.60 (m, 2H), 2.41-2.38 (m, 3H), 2.21-2.15 (m, 5H), 2.09-1.98 (m, 5H), 1.92-1.76 (m, 8H), 1.67-1.64 (m, 5H), 1.56-1.47 (m, 8H), 1.38-1.36 (m, 6H), 1.29 (brs, 9H), 0.85-0.79 (m, 1H), 0.56-0.52 (m, 2H), 0.15-0.11 (m, 2H). $^{13}$C NMR (100 MHz, CDCl$_3$): δ 173.5, 168.9, 168.63, 168.57, 168.4, 159.3, 159.1, 152.6, 143.5, 142.0, 139.94, 139.90, 130.7, 128.84, 128.82, 127.58, 127.55, 126.5, 124.32, 124.30, 119.2, 118.1, 118.0, 91.8, 71.0, 70.9, 70.7, 70.1, 62.4, 59.4, 59.3, 59.1, 58.7, 58.3, 57.3, 51.8, 49.80, 49.76, 48.6, 48.3, 47.5, 47.3, 45.2, 43.9, 42.9, 39.6, 39.2, 39.1, 36.3, 36.2, 35.4, 35.0, 33.13, 33.09, 32.9, 32.8, 32.64, 32.60, 31.9, 29.4, 29.1, 28.9, 27.3, 26.70, 26.65, 26.6, 26.5, 26.1, 26.00, 25.96, 25.9, 23.4, 22.6, 21.7, 15.5, 9.5, 4.0, 3.8. 19F NMR (376 MHz, CDCl$_3$): δ −92.60, −93.23, −100.30, −100.93. HRMS (ESI) m/z calcd. for C$_{67}$H$_{97}$F$_2$N$_{10}$O$_{10}$ [M+H]+: 1239.7357, found: 1239.7338; calcd. for C$_{67}$H$_{96}$F$_2$N$_{10}$NaO$_{10}$ [M+Na]+: 1261.7177, found: 1261.7164; calcd. for C$_{67}$H$_{98}$F$_2$N$_{10}$O$_{10}$ [M+2H]2+: 620.3718, found: 620.3594; calcd. for C$_{67}$H$_{97}$F$_2$N$_{10}$NaO$_{10}$ [M+H+Na]2+: 631.3627, found: 631.3517. HPLC purity: 99.96%. Rt: 7.300 min.

Bivalent Ligand VZMC019

This target compound was prepared in a similar way as VZMC013, by coupling the 2'-aminoethyl maraviroc precursor 24 with 30c. White solid. Yield: 55%. Compound VZMC019 was converted to its hydrochloride salt for biological assays. Hydrochloride salt. 1H NMR (400 MHz, DMSO-d6): δ 11.27 (s, 1H), 10.10 (s, 1H), 9.34 (s, 1H), 8.84 (s, 1H), 8.54 (d, J=8.36 Hz, 1H), 8.28 (d, J=8.40 Hz, 1H), 8.14 (t, J=5.64 Hz, 1H), 8.07 (t, J=5.80 Hz, 1H), 7.62 (d, J=8.56 Hz, 2H), 7.33 (d, J=8.52 Hz, 2H), 6.72 (d, J=8.12 Hz, 1H), 6.65 (d, J=8.24 Hz, 1H), 6.18 (s, 1H), 4.88-4.82 (m, 1H), 4.76 (d, J=7.72 Hz, 1H), 4.50-4.40 (m, 1H), 4.23-4.21 (m, 1H), 4.16 (s, 2H), 4.05 (s, 2H), 3.97 (d, J=3.16 Hz, 3H), 3.85 (d, J=5.60 Hz, 1H), 3.73 (brs, 1H), 3.57-3.48 (m, 4H), 3.18-3.08 (m, 6H), 3.05-3.03 (m, 2H), 2.97-2.92 (m, 3H), 2.89-2.83 (m, 2H), 2.75-2.69 (m, 5H), 2.47-2.42 (m, 3H), 2.40-2.34 (m, 2H), 2.28-2.21 (m, 3H), 2.17-2.09 (m, 4H), 2.05-2.02 (m, 1H), 1.89-1.71 (m, 5H), 1.67-1.55 (m, 2H), 1.53-1.43 (m, 6H), 1.29-1.27 (m, 8H), 1.08-1.04 (m, 1H), 0.70-0.65 (m, 1H), 0.62-0.57 (m, 1H), 0.53-0.48 (m, 1H), 0.44-0.38 (m, 1H). $^{13}$C NMR (100 MHz, DMSO-d6): δ 173.5, 168.8, 168.4, 168.3, 167.8, 159.7, 151.5, 142.1, 141.3, 138.0, 137.1, 129.6, 126.6, 120.6, 119.8, 119.2, 117.9, 89.7, 70.7, 70.6, 70.32, 70.28, 69.7, 61.5, 61.2, 60.3, 56.6, 50.3, 49.8, 48.6, 47.0, 46.7, 46.5, 45.6, 40.8, 40.1, 38.14, 38.09, 32.9, 32.2, 32.0, 30.6, 29.4, 28.9, 28.8, 25.59, 25.50, 25.47, 24.33, 24.31, 23.8, 23.7, 23.49, 23.47, 23.0, 21.5, 11.7, 11.5, 5.7, 5.1, 2.6. 19F NMR (376 MHz, DMSO-d6): δ −89.77, −90.40, −98.68, −99.30. 19F NMR (376 MHz, CDCl$_3$): δ −92.66, −93.29, −100.32, −100.95. HRMS (ESI) m/z calcd. for C$_{63}$H$_{89}$F$_2$N$_{10}$O$_{10}$ [M+H]+: 1183.6731, found: 1183.6692; calcd. for C$_{63}$H$_{88}$F$_2$N$_{10}$NaO$_{10}$ [M+Na]+: 1205.6551, found: 1205.6507; calcd. for C$_{63}$H$_{90}$F$_2$N$_{10}$O$_{10}$ [M+2H]2+: 592.3405, found: 592.3318; calcd. for C$_{63}$H$_{89}$F$_2$N$_{10}$NaO$_{10}$ [M+H+Na]$^{2+}$: 603.3314, found: 603.3225. HPLC purity: 99.96%. Rt: 6.867 min.

Preparation of the Monovalent Ligand VZMC014, VZMC018 and VZMC020

2-(2-(Methylamino)-2-oxoethoxy)acetic acid (31). To a 2 M solution of methanamine in THF (27.5 mL, 55 mmol) was added diglycolic anhydride (5.80 g, 50 mmol) in portions. After being stirred for 15 h at room temperature, the reaction mixture was concentrated under reduced pressure. The residue was further recrystallized with methanol to afford 31 as a faint yellow solid (6.11 g, 83%). 1H NMR (400 MHz, DMSO-d6): δ 12.80 (brs, 1H, exchangeable), 7.76 (s, 1H, exchangeable), 4.09 (s, 2H), 3.94 (s, 2H), 2.62 (d, J=4.80 Hz, 3H). $^{13}$C NMR (100 MHz, DMSO-d6): δ 171.3, 169.1, 70.1, 67.8, 25.1. C$_5$H$_9$NO$_4$ (147.0532).

Benzyl (7-(2-(2-(methylamino)-2-oxoethoxy)acetamido) heptyl)carbamate (32a). The title compound was prepared following the general amide coupling procedure by reacting acid 31 with the Cbz-protected amine 26a. White solid. Yield: 47%. 1H NMR (400 MHz, DMSO-d6): δ 7.99-7.96 (m, 2H, exchangeable), 7.38-7.28 (m, 5H), 7.19 (brs, 1H, exchangeable), 5.00 (s, 2H), 3.91 (s, 2H), 3.90 (s, 2H), 3.10 (q, J=6.80 Hz, 2H), 2.98 (q, J=6.80 Hz, 2H), 2.65 (d, J=8.80 Hz, 3H), 1.46-1.38 (m, 4H), 1.25 (brs, 6H). $^{13}$C NMR (100 MHz, DMSO-d6): δ 168.8, 168.2, 156.0, 137.3, 128.2, 127.6, 70.2, 65.0, 38.1, 29.3, 29.1, 28.4, 26.3, 26.1, 25.0. C$_{20}$H$_{31}$N$_3$O$_5$ (393.2264). Benzyl (9-(2-(2-(methylamino)-2-oxoethoxy)acetamido)nonyl)carbamate (32b).

This title compound was prepared in a similar way as 32a, by reacting acid 31 with amine 26b. White solid. Yield: 36%. 1H NMR (400 MHz, DMSO-d6): δ 8.02-7.97 (m, 2H, exchangeable), 7.39-7.29 (m, 5H, Ph-H), 7.21 (t, J=5.44 Hz, 1H, exchangeable), 5.01 (s, 2H), 3.92 (s, 2H), 3.91 (s, 2H), 3.11 (q, J=6.76 Hz, 2H), 2.98 (q, J=6.68 Hz, 2H), 2.66 (d, J=4.72 Hz, 3H), 1.45-1.38 (m, 4H), 1.25 (brs, 10H). HRMS (ESI) m/z calcd. for C$_{22}$H$_{35}$N$_3$NaO$_5$ [M+Na]+: 444.2474, found: 444.2461.

Benzyl (5-(2-(2-(methylamino)-2-oxoethoxy)acetamido) pentyl)carbamate (32c). This title compound was prepared in a similar way as 32a, by reacting acid 31 with amine 26c. White solid. Yield: 27%. 1H NMR (400 MHz, DMSO-d6): δ 8.02-7.97 (m, 2H, exchangeable), 7.39-7.29 (m, 5H, Ph-H), 7.23 (t, J=5.44 Hz, 1H, exchangeable), 5.01 (s, 2H), 3.92 (s, 2H), 3.91 (s, 2H), 3.11 (q, J=6.64 Hz, 2H), 2.99 (q, J=6.68 Hz, 2H), 2.66 (d, J=4.68 Hz, 3H), 1.47-1.38 (m, 4H), 1.29-1.21 (m, 2H). C$_{18}$H$_{27}$N$_3$O$_5$ (365.1951).

Compounds 33a-c and 34a-c were prepared as previously reported.32, 34

Monovalent Ligand VZMC014

The target compound was prepared following the general amide coupling procedure by reacting the 2'-aminoethyl maraviroc precursor 24 with 34a. White solid. Yield: 46%. Hydrochloride salt. 1H NMR (400 MHz, $CD_3OD$): δ 7.88 (brs, 1H), 7.57 (brs, 1H), 7.25-7.21 (m, 2H), 7.15 (brs, 1H), 4.99-4.95 (m, 1H), 4.43-4.30 (m, 1H), 4.24-4.13 (m, 1H), 3.92 (s, 3H), 3.90-3.88 (m, 2H), 3.57-3.48 (m, 2H), 3.38-3.29 (m, 2H), 3.16-3.08 (m, 7H), 3.03-2.98 (m, 2H), 2.89-2.84 (m, 2H), 2.76 (s, 1H), 2.69 (s, 3H), 2.41-2.32 (m, 3H), 2.26 (s, 4H), 2.19-2.02 (m, 2H), 1.96-1.87 (m, 4H), 1.76-1.67 (m, 4H), 1.64-1.61 (m, 2H), 1.43 (brs, 3H), 1.25 (s, 7H), 1.12-1.19 (m, 1H), 1.02 (t, J=6.68 Hz, 4H). $^{13}C$ NMR (100 MHz, $CD_3OD$): δ 176.6, 172.1, 171.9, 171.5, 171.4, 153.4, 144.2, 129.6, 128.3, 127.7, 112.6, 71.55, 71.52, 71.48, 70.1, 66.9, 60.9, 60.4, 59.8, 58.1, 52.7, 50.1, 45.0, 43.7, 42.2, 40.1, 39.7, 38.2, 37.72, 37.69, 36.4, 33.9, 33.8, 30.40, 30.38, 30.0, 28.5, 27.9, 27.3, 27.2, 27.15, 27.06, 27.0, 25.9, 22.3, 15.4, 14.0. 19F NMR (376 MHz, $CD_3OD$): δ −93.06, −93.68, −102.67, −103.26. HRMS (ESI) m/z calcd. for $C_{46}H_{72}F_2N_9O_7[M+H]+$: 900.5523, found: 900.2709. HPLC purity: 99.72%. Rt: 6.583 min.

Monovalent Ligand VZMC018

This target compound was prepared in a similar way as VZMC014, by coupling the 2'-aminoethyl maraviroc precursor 24 with 34b. White solid. Yield: 35%. Hydrochloride salt. 1H NMR (400 MHz, $CDCl_3$): δ 8.19 (t, J=5.76 Hz, 1H), 7.38-7.35 (m, 2H), 7.30-7.28 (m, 3H), 7.11 (t, J=5.72 Hz, 1H), 6.68-6.50 (m, 2H), 6.31-6.29 (m, 1H), 5.17-5.11 (m, 1H), 4.36-4.26 (m, 1H), 4.05 (s, 2H), 4.03 (s, 2H), 3.99 (s, 3H), 3.77 (q, J=5.88 Hz, 2H), 3.39-3.34 (m, 4H), 3.29 (q, J=6.80 Hz, 3H), 3.03-2.98 (m, 3H), 2.89-2.86 (m, 3H), 2.42-2.38 (m, 2H), 2.27 (s, 1H), 2.23-2.11 (m, 6H), 2.07-1.93 (m, 6H), 1.93-1.83 (m, 4H), 1.38 (d, J=6.80 Hz, 6H), 1.29-1.21 (m, 16H). $^{13}C$ NMR (100 MHz, $CDCl_3$): δ 173.4, 173.1, 169.2, 168.7, 168.6, 168.5, 168.4, 128.9, 127.7, 126.5, 77.2, 71.3, 71.24, 71.22, 70.8, 70.7, 58.4, 51.8, 47.4, 42.9, 39.20, 39.18, 39.1, 36.3, 36.1, 32.8, 29.71, 29.68, 29.50, 29.45, 29.1, 28.94, 28.92, 26.7, 26.64, 26.62, 26.58, 26.02, 25.95, 25.9, 25.7, 21.7. 19F NMR (376 MHz, $CDCl_3$): δ −92.70, −93.33, −100.45, −101.05. HRMS (ESI) m/z calcd. for $C_{48}H_{76}F_2N_9O_7[M+H]+$: 928.5836, found: 928.5843. HPLC purity: 95.89%. Rt: 8.062 min.

Monovalent Ligand VZMC020

This target compound was prepared in a similar way as VZMC014, by coupling the 2'-aminoethyl maraviroc precursor 24 with 34c. White solid. Yield: 21%. Hydrochloride salt. 1H NMR (400 MHz, DMSO-d6): δ 11.45 (brs, 1H), 10.11 (s, 1H), 8.56-8.54 (m, 1H), 8.14 (s, 1H), 8.06-8.01 (m, 2H), 7.62 (d, J=8.60 Hz, 2H), 7.35-7.32 (m, 3H), 7.22 (brs, 2H), 7.10 (brs, 2H), 4.88-4.82 (m, 1H), 4.49 (brs, 1H), 4.24-4.23 (m, 1H), 4.15 (s, 2H), 4.05 (s, 2H), 3.92 (s, 3H), 3.16-3.09 (m, 4H), 2.97-2.92 (m, 2H), 2.76 (brs, 3H), 2.66 (d, J=4.68 Hz, 2H), 2.56-2.55 (m, 1H), 2.46-2.33 (m, 3H), 2.27-2.13 (m, 6H), 2.08-2.00 (m, 2H), 1.90-1.75 (m, 3H), 1.70-1.56 (m, 2H), 1.51-1.42 (m, 3H), 1.30-1.25 (m, 7H), 1.05 (d, J=6.12 Hz, 1H). $^{13}C$ NMR (100 MHz, DMSO-d6): δ 168.9, 168.4, 168.3, 142.1, 141.3, 129.6, 120.5, 89.7, 70.4, 70.3, 69.6, 64.9, 61.6, 56.7, 50.3, 46.5, 45.6, 38.1, 38.04, 38.01, 29.4, 28.90, 28.89, 28.8, 25.1, 23.79, 23.75, 23.7, 23.4, 23.0, 21.2, 15.1, 11.5, 5.7, 5.1, 3.2, 2.6. 19F NMR (376 MHz, DMSO-d6): δ −89.81-90.42, −98.82, −99.46. $C_{44}H_{67}F_2N_9O_7$ (871.5132). HPLC purity: 98.62%. Rt: 6.589 min.

In vitro MOR radioligand binding assay The competition binding assay was conducted using monoclonal mouse MOR expressed in Chinese hamster ovary (CHO) cell lines. In this assay, 30 μg of membrane protein was incubated with the radioligand [³H] naloxone in the presence of different concentrations of tested compounds in TME buffer (50 mM Tris, 3 mM $MgCl_2$, and 0.2 mM EGTA, pH 7.4) for 1.5 h at 30° C. The bound radioligand was separated by filtration using a Brandel harvester. Specific (i.e., opioid receptor-related) binding to the MOR was determined as the difference in binding obtained in the absence and presence of 5 μM of DAMGO. The $IC_{50}$ values were determined and converted to Ki values using the Cheng-Prusoff equation: Ki=$IC_{50}$/[1+([L*]/KD)], where [L*] is the concentration of the radioligand and KD is the KD of the radioligand was determined.73

[³¹S]-GTPγS Functional Assay

[³⁵S]-GTPγS functional assays was conducted in the mouse MOR cell membrane used for the receptor binding assays. Membrane protein (10 μg) was incubated with varying concentrations of test compounds, GDP (15 μM), and 80 μM [35S]-GTPγS in assay buffer for 1 h at 30° C. Nonspecific binding was determined with 10 μM unlabeled GTPγS. DAMGO (5 μM) was included in the assay for a maximally effective concentration of a full agonist for the MOR. After incubation, the bound radioactive ligand was separated from the free radioligand by filtration through a GF/B glass fiber filter paper and rinsed three times with ice-cold wash buffer (50 mM Tris-HCl, pH 7.2) using the Brandel harvester. The results were determined by utilizing a scintillation counter. All assays were determined in triplicate and repeated at least three times. Percent DAMGO stimulated [35S]-GTPγS binding was defined as (net-stimulated binding by ligand/net-stimulated binding by 3 μM DAMGO)×100%.

Calcium Mobilization Assay in mMOR-CHO Cells

A CHO cell line stably expressing the mouse mu opioid receptor (mMOR-CHO) was used for this assay. The cells were transfected with Gαqi5 for 4 h and then plated (10,000 cells/well) to black 96-well plates with clear bottoms (Greiner Bio-One). After 24 h of incubation, the culture medium was removed, and the cells were washed with assay buffer (50 mL of HBSS, 1 mL of HEPES, 250 μL of probenecid, 50 μL of 1 mM $CaCl_2$, and 50 μL of 1 mM $MgCl_2$). The tested compounds were dissolved in DMSO as a stock solution for the assay (1 M). For agonist assays, cells were then incubated with 50 μL/well loading buffer (6 mL of assay buffer, 24 μL of Fluo4-AM solution (Invitrogen), and 12 μL of probenecid solution) for 60 min. Following incubation, different concentrations of the tested compounds were added by a FlexStation3 microplate reader (Molecular Devices) and read at ex494/em516. Each concentration was run in triplicate. For antagonism studies, the cells were incubated with the same loading buffer as the agonist assay for 60 min. Then, different concentrations of the tested compounds (20 μL/well) were manually added to each well followed by another 15 min of incubation. After that, the solution of DAMGO in assay buffer (500 nM) or just assay buffer (blank) was added by a FlexStation3 microplate reader (Molecular Devices) and read at ex494/em516. Each concentration was run in triplicate. The corresponding $IC_{50}$ value of each compound was calculated by non-linear regression using GraphPad Prism 8.0.1 (GraphPad Software, San Diego, CA).

In Vitro CCR5 Radioligand Binding Assay

The CCR5 competitive radioligand binding assay was conducted following previously reported studies.74, 75 Rhesus macaque chemokine CCR5 receptors expressed in Chem-1 cells are assayed in modified HEPES buffer (50 mM HEPES, 1 mM $CaCl_2$, 5 mM $MgCl_2$, 0.2% BSA, pH 7.4). 3 μg of membrane protein was incubated with 0.10 nM [$^{125}$I]MIP-1α in the presence of six concentrations of tested compounds (10 μM, 1 μM, 0.1 μM, 10 nM, 1 nM, and 0.1 nM) for 90 min at 25° C. Non-specific binding is estimated in the presence of 0.1 μM MIP-1β. Membranes are filtered and washed, and the filters are then counted to determine [125I]MIP-1α specifically bound, which specific binding was defined as 85% as a historical value. The $IC_{50}$ values were determined and converted to Ki values using the Cheng-Prusoff equation: $Ki=IC_{50}/[1+([L^*]/KD)]$, where [L*] is 0.10 nM and KD is 0.31 nM (historical value).

Calcium Mobilization Assay in HOS-CCR5 Cells

HOS-CCR5 cells were transfected with Gqi5 pcDNA16 using Lipofectamine 2000 (Invitrogen) according to the manufacturer's recommended procedure and maintained in RPMI 1640 supplemented with 10% fetal bovine serum, 100 μg/mL penicillin, 100 μg/mL streptomycin, and 1 mg/mL G418 at 37° C. and 5% C02. 48 h after transfection, a total of 2,500,000 cells were spun down and brought back up in 8 mL of 50:1 HBSS: HEPES assay buffer. Cells were then plated at 25,000 cells per well into a clear bottom, black 96-well plate (Greiner Bio-one) and 50 μL of Fluo4 loading buffer [40 μL of 2 μM Fluo4-AM (Invitrogen), 100 μL of 2.5 mM probenecid, in 5 mL of assay buffer] was added to bring the volume up to 130 μL. After incubating for 45 min, 50 μL of varying concentrations of tested compounds were added and the plate was incubated for an additional 15 min. Plates were then read on a FlexStation3 microplate reader (Molecular Devices) at 494/516 ex/em for a total of 120 s. After 16 s of reading, 20 μL of 200 nM CCL5 (Biosource) in assay buffer, or assay buffer alone, was added to the wells to bring the total volume up to 200 μL. The changes in calcium mobilization were monitored and peak height values were obtained using SoftMaxPro software (Molecular Devices). Non-linear regression curves and $IC_{50}$ values were generated using GraphPad Prism 8.0.1 (GraphPad Software, San Diego, CA). All experiments were repeated at least three times.

Anti-HIV-1BaL Activity (Reverse Transcriptase Activity) and Cytotoxicity Assays in GHOST CCR5 Cells 100 μL of GHOST CCR5 cells at a density of 1×104 cells/well in 10% complete DMEM (10% FBS with 1% L-glutamine and 1% Penicillin/Streptomycin) media were plated in a 96-well flat bottom plate and incubated for 24 h at 37° C./5% $CO_2$. Following the incubation, 100 μL of each compound at 6 concentrations were added in triplicate to both efficacy and toxicity plates followed by 100 μL of HIV-1BaL at a pre-determined titer to the plates being evaluated for efficacy and 50 μL of complete DMEM to the plates being evaluated for cytotoxicity. The cultures were incubated for 6 days at 37° C./5% $CO_2$. Following the incubation, 50 μL of cell culture supernatant was removed from the wells of the efficacy plates for subsequent evaluation of virus content by reverse transcriptase activity assay. The toxicity plates being evaluated for cytotoxicity were stained with XTT.

RT activity ($EC_{50}$ values) was measured using standard radioactivity incorporation polymerization assay. 1 μL of titrated thymidine triphosphate (TTP) at 1 Ci/mL was used per enzyme reaction. Poly rA and oligo dT were prepared at concentrations of 0.5 mg/mL and 1.7 Units/mL, respectively, from a stock solution which was kept at −20° C. The RT reaction buffer was prepared fresh and consists of 125 μL of 1M EGTA, 125 μL of dH2O, 125 μL of 20% Triton X-100, 50 μL of 1M Tris (pH 7.4), 50 μL of 1M DTT, and 40 μL of 1 M MgCl2. For each reaction, 1 μL of TTP, 4 μL of dH2O, 2.5 μL of rAdT and 2.5 μL of reaction buffer were mixed. 10 μL of this reaction mixture was placed in a round bottom microtiter plate with 15 μL of virus containing supernatant. The plate was incubated at 37° C. in a humidified incubator for 60-90 min. Following the incubation, 10 μL of the reaction volume was spotted onto a DEAE filter mat (Perkin Elmer, catalog #1450-522) in the appropriate plate format, washed 5 times for 5 min each in a sodium (150 mM) citrate (15 mM) buffer (Invitrogen, catalog #15557-036), 2 times for 1 min each in deionized water (ImQuest), 2 times for 1 min each in 70% reagent alcohol (Fisher, catalog #L-7168), and then air dried. The dried filtermat was placed in a plastic sleeve and 4 mL of Opti-Fluor O (Perkin Elmer, catalog #1205-440) scintillation fluid was added to each sleeve. Incorporated radioactivity was quantified using a Wallac 1450 Microbeta Trilux liquid scintillation counter. $TC_{50}$ values for the tested compounds were derived by measuring the reduction of the tetrazolium dye XTT (2,3-bis(2-methoxy-4-nitro-5-sulfophenyl)-5-[(phenylamino)carbonyl]-2H-tetrazolium hydroxide). XTT in metabolically active cells is metabolized by the mitochondrial enzyme NADPH oxidase to a soluble formazan product. XTT solution was prepared as a stock of 1 mg/mL in RPMI-1640 without additives. Phenazine methosulfate (PMS) solution was prepared at 0.15 mg/mL in DPBS and stored in the dark at −20° C. XTT/PMS stock was prepared immediately before use by adding 40 μL of PMS per mL of XTT solution. 50 μL of XTT/PMS was added to each well of the plate and the plate was incubated for 4 h at 37° C. The plates were sealed and inverted several times to mix the soluble formazan product and the plate was read at 450 nm (650 nm reference wavelength) with a Molecular Devices SPECTRAMAX® Plus 384 96 well format spectrophotometer.

HIV-1BaL Infection Assay in MOR-CCR5 Co-Expressed TZM-b1 Cells

HIV-1BaL.01 was kindly donated and expanded in Phytohemagglutinin (PHA)-activated Peripheral Blood Mononuclear Cells (PBMCs). The amount of viral particles was determined by commercial ELISA for p24 capsid antigen (Zeptometrix) and aliquots were stored at −80° C. The TZM-b1, a cell line contained integrated copies of luciferase under control of the HIV-1 long-terminal repeat (LTR), were kindly donated. Cells were transfected with plasmid containing GFP-tagged human opioid receptor mu 1 gene (OPRM1; Origene) or with the original empty vector also containing GFP (control plasmid; Origene) and selected for 2 weeks with 2 mg/ml G418 (Invivogen) in DMEM (Hyclone) supplemented with 1×MEM Non-essential amino acids (Gibco), 10% heat-inactivated FBS (Hyclone) and 100 U Penicillin-0.1 mg/ml Streptomycin (Sigma). Then, GFP+ cells were sorted out twice by flow cytometry (BD-FACSAria model, Becton-Dickinson) and maintained in the conditions mentioned above with 800 μg/ml G418. For the infection, cells were detached from 25 cm2 flasks with 0.25% Trypsin (Sigma), washed by centrifugation (400 g—10 mins) and viable cells determined by Trypan blue (Sigma) exclusion. Cells were added in 96-wells black walled plate at 1.5×104 cells/well in 90 μL volume of DMEM containing 10% heat-inactivated FBS and 100 U Penicillin-0.1 mg/ml Streptomycin. After 6-10 h incubation at 37° C. in 5% C02:95% air, the bivalent compound VZMC013 was added 1 h before infection with HIV-1BaL at 460 pg p24/well, in a final volume of 100 μL per well. Luciferase activity was evaluated following the addition of 100 μL/well of 2× luciferase substrate containing lysis buffer (BRIGHT-GLO™ Luciferase Substrate, Promega) after 2-3 days of infection.

Luminescence, reported as relative luminescence units (RLU), was evaluated in PHERASTAR® FS plate reader and results expressed as percentage of inhibition relative to vehicle-treated, infected cells (100% infection).

HIV-1-Luc Infection Assay in Peripheral Blood Mononuclear Cells (PBMCs)

Isolated human PBMCs were obtained commercially from the New York Blood Bank and exempt from Human Subjects criteria (NIH Exemption 4: website located at nih.gov/sites/default/files/ exemption_infographic_v7_508c-3-21-19.pdf). The adult PBMCs are publicly available and no information or identifiers are provided so subjects cannot be identified. HIV-1BaL env-pseudotyped Luciferase viruses were generated by co-transfecting HEK293TT cell line (kindly donated) with plasmids containing expression vectors for HIV-1BaL.01 env and for HIV-1NL4-3 delta-env with Luciferase inserted into nef gene. After 3 days in culture, supernatants were harvested, floating cells removed by centrifugation, HIV-1 p24 Ag measured by commercial ELISA (Zeptometrix), and viral aliquots stored at −80° C. Both plasmids were donated.

PBMCs were isolated from buffy coats of healthy blood donors by centrifugation in Ficoll gradient (MP Biomedicals). Viable cells, determined by Trypan blue exclusion, were stimulated, or not, for 2 days with 5 μg/mL PHA (Sigma). Non-PHA stimulated cells were distributed in 96-wells black walled plates at 2×105 per well in RPMI-1640 medium supplemented with 1 mM Sodium Pyruvate (Gibco), 1×MEM Non-essential amino acids, 10% heat-inactivated FBS, 100 U Penicillin-0.1 mg/ml Streptomycin and 20 U/mL recombinant human Interleukin-2 (Peprotech). Cells were infected with HIV-1BaL.01 env-pseudotyped Luc virus at 1.5 ng p24/well in a final volume of 100 μL and uninfected cells served as a negative control. The bivalent compound VZMC013 was added one hour before infection and kept in the culture.

After 2 days of infection, 100 μL of 2× Luciferase Substrate containing lysing buffer (BRIGHT-GLO™ Luciferase Assay System, Promega) were added per well, plate was agitated for 2 mins (700 rpm) and Luminescence was evaluated using a PHERASTAR® FS plate reader (BMG Labtech).

HIV-1 Infection Assay in PHA-Stimulated PBMC Cells

In a 24-well plate, PHA-stimulated PBMC cells from healthy donors were infected by incubation with the HIV-1BaL.01 env-pseudotyped Luc virus. A concentration of HIV-1 p24 50 pg/106 cells was used, and uninfected cells served as a negative control. Cells were treated with and without morphine or DAMGO (10 nM) along with bivalent compound VZMC013 (100 nM) 3 days before HIV-1 infection. After approximately 18-20 h, the supernatant was removed and stored at −80° C., cells were rinsed twice with PBS and lysed. The lysate was subsequently tested for the relative Tat protein expression by using a luciferase assay system (Promega). Luciferase activity was measured using a PHERASTAR® FS plate reader (BMG Labtech).

Molecular Docking and Molecular Dynamics Simulation

To generate the MOR-CCR5 heterodimer, the monomeric crystal structures of CCR5 (PDB ID: 4MBS)44 and MOR (PDB ID: 4DKL)46 were downloaded from the Protein Data Bank.76 Prior to performing the molecular docking, other parts of the two crystal structures were removed with the exception of the N-terminus, the seven transmembrane helices, and the C-terminus. In addition, the missing residues in intracellular loop 3 (ICL3) of 4MBS and ICL3 of 4DKL were modeled by Sybyl 8.0. Naltrexone was first docked into the MOR to obtain its monomeric complex with MOR, named as MOR_naltrexone complex. Remaining the CCR5 and original ligandmaraviroc obtained the CCR5 monomer complexing with maraviroc, referred to CCR5_maraviroc complex. Afterward, Hex 8.0.0 was applied to dock the two complexes together to build the heterodimer model.77 The process included four steps: (1) CCR5_maraviroc and MOR_naltrexone complexes were put together and moved close enough to each other. (2) CCR5_maraviroc complex was fixed and its TM1/2 was selected as the dimer interface. (3) MOR_naltrexone complex was rotated to find its dimer interface at TM5/6 and further to interact with TM1/2 of the CCR5. (4) the new coordinates of CCR5_maraviroc and MOR_naltrexone complexes were obtained and saved as the starting model of the MOR-CCR5 heterodimer complexing with their respective ligands.

The above heterodimer model was inserted into a 1-palmitoyl-2-oleoylphosphatidylcholine (POPC) lipid membrane and solvated by TIP3 water molecules to conduct an energy minimization determination using Amber14.0. The energy minimization process included three steps: (1) restraining the ligands, the heterodimer complex, and the lipid membrane to minimize the water molecules and ions; (2) restraining the backbone atoms of the heterodimer, the ligands, and the lipid membrane to minimize the protein side chains, the water molecules, and ions; (3) energy minimizing the whole system without restraint. The energy minimized heterodimer model was applied as the starting structure to build the bivalent ligand VZMC013 into the binding site of the MOR-CCR5 heterodimer.

Figure 2C:
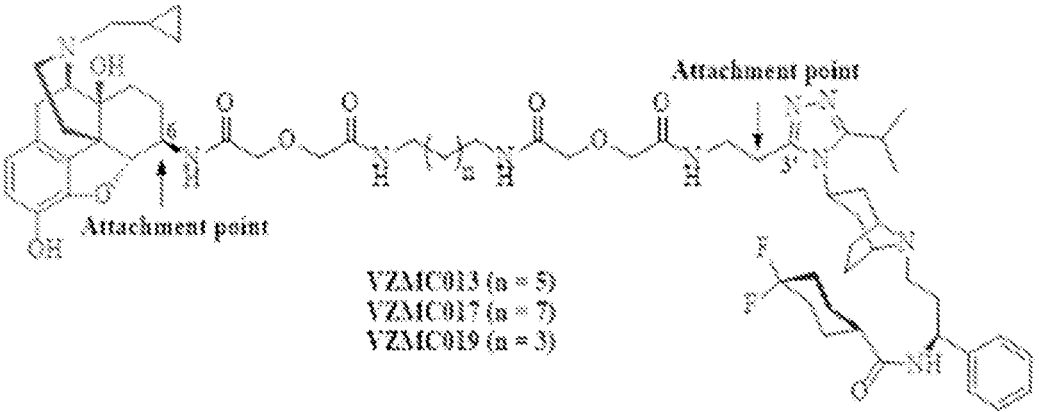

In the energy minimized heterodimer model, the CCR5 pharmacophore maraviroc and the MOR pharmacophore naltrexone were both in their respective binding pockets. The molecular graphics software Sybyl-X 8.0 (TRIPOS Inc., St. Louis, MO) was applied to connect the two pharmacophores by the spacer displayed in FIG. 2C.

Finally, the MOR-CCR5 heterodimer complexing with the bivalent ligand VZMC013 was obtained and named as MOR-CCR5_VZMC013 complex. With the MOR-CCR5_VZMC013 complex in hand, the bivalent ligand VZMC013 was firstly extracted from the complex by Sybyl-X 8.0 (TRIPOS Inc., St. Louis, MO) and then VZMC013 was examined with the correct atom type, bond type and hydrogen atoms. Next, the structure of VZMC013 was optimized to its minimum energy conformation by Gaussian 03. After that, VZMC013 was submitted to the antechamber program in AMBER 14 to form its restrained electrostatic potential (RESP) charges descriptors and other force field parameters. In the following, a system included the MOR-CCR5_VZMC013 complex, the 1-palmitoyl-2-oleoylphosphatidylcholine (POPC) lipid membrane, the TIP3 water box, and 0.15 M sodium and chloride ions was built by the CHARMM-GUI website service. Meanwhile, the input files of the MD simulations were also generated. MD simulations were performed by GROMACS (ver. 2018.2) package (www.gromacs.org). The Amber 03 force field was selected for the simulations. The 20000 steps of the steepest-descent energy minimization were initially applied to the system. After that, the system was heated to 310 K via two steps. First, heating from 0 K to 100 K under a constant volume ensemble (NVT) for 0.5 ns. Second, heating from 100 K to 310 K under a constant pressure ensemble (NPT) for another 1.0 ns. Subsequently, a 100 ns MD simulation was conducted using the NPT (P=105 Pa, T=310 K)

ensemble. The long-range electrostatic interactions were computed using the Particle Mesh Ewald (PME) method. A smooth cutoff of 10 Å was used to calculate the non-bonded van der Waals interactions. The periodic boundary conditions were applied during the MD simulations. The snapshots were collected at 2 fs intervals.

Abbreviations

MOR, mu opioid receptor; CCR5, C—C chemokine receptor type 5; HIV, human immunodeficiency virus; GPCRs, G-protein-coupled receptors; CCL5, C—C motif chemokine ligand 5; PBMC, peripheral blood mononuclear cells; PHA, phytohemagglutinin; AIDS, acquired immune deficiency syndrome; OUD, opioid use disorder; DAMGO, [D-Ala$^2$-MePhe$^4$-Gly(ol)$^5$]enkephalin; CHO, Chinese hamster ovary; β-FNA, β-funaltrexamine; TM, transmembrane; PDB, protein data bank; Cbz, carboxybenzyl; Fmoc, fluorenylmethyloxycarbonyl; TsOH, toluenesulfonic acid; HOBt, hydroxybenzotriazole; EDCI, 1-Ethyl-3-(3-dimethylaminopropyl)carbodiimide; SEM, standard error of the mean; MIP-1β, macrophage inflammatory protein 1 beta; RT, reverse transcriptase; TI, therapeutic index; LTR, long-terminal repeat; Tat, trans-activator of transcription; luciferase gene, Luc; MD, molecular dynamics; ECL, extracellular loop; ICL, intracellular loops; RMSD, root-mean-square deviation; RMSF, root-mean-square fluctuation; HRMS, high resolution mass spectrum; TOF, time of flight; TMS, tetramethylsilane; $^1$H NMR, proton nuclear magnetic resonance; $^{13}$C NMR, carbon nuclear magnetic resonance; $^{19}$F NMR, fluorine nuclear magnetic resonance; HPLC, high performance liquid chromatography.

Example 2. Synthesis of Other Bivalent Ligands

The following Schemes show synthetic methods that are used to prepare other ligands.

Scheme 6

Scheme 7

EDCI/HOBt/TEA/DMF
then diglycolic anhydride/THF

EDCI/HOBt/TEA/DMF

Scheme 8

EDCI/HOBt/TEA/DMF
then TFA/DCM

-continued

Scheme 9

91 92

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A bivalent ligand having Formula I:

Formula I where L is where n ranges from 0 to 12, * indicates a point of attachment to naltrexone; and
** indicates a point of attachment to maraviroc;
or where n ranges from 0 to 12, * indicates a point of attachment to naltrexone; and
** indicates a point of attachment to maraviroc;
or where n ranges from 0 to 12, * indicates a point of attachment to naltrexone; and
** indicates a point of attachment to maraviroc;
or where n ranges from 0 to 12, * indicates a point of attachment to naltrexone; and
** indicates a point of attachment to maraviroc;
or where n ranges from 0 to 12, * indicates the point of attachment to naltrexone; and
** indicates the point of attachment to maraviroc.

2. The bivalent ligand of claim 1, wherein the bivalent ligand is where n is 3, 5 or 7.

3. The bivalent ligand of claim 2, wherein n is 5.

4. A lyophilized preparation comprising at least one bivalent ligand of claim 1.

5. The lyophilized preparation of claim 4, wherein the at least one bivalent ligand is labeled with at least one detectable label.

6. A preparation comprising at least one bivalent ligand of claim 1 and a liquid carrier.

7. The preparation of claim 6, wherein the at least one bivalent ligand is labeled with at least one detectable label.

8. A method of detecting a MOR-CCR5 heterodimer, comprising
contacting the MOR-CCR5 heterodimer with bivalent ligand of claim 1 under conditions that permit the bivalent ligand to bind to and form a complex with the MOR-CCR5 heterodimer, and
detecting the complex.

9. The method of claim 8, wherein the bivalent ligand is labeled with at least one detectable label.

10. The method of claim 9, wherein the method is an in vitro method or an in vivo method.

11. The method of claim 9, wherein the MOR-CCR5 heterodimer is present on a cell.

12. A method of preventing or treating, in a subject in need thereof, a disease or condition characterized by the formation of MOR-CCR5 heterodimers, comprising
administering to the subject a therapeutically effective amount of at least one bivalent ligand of claim 1.

13. The method of claim 12, wherein the disease or condition is a neurological disease or condition selected from the group consisting of neuro-AIDS, dementia, neu-rodegradation, multiple sclerosis, neuropathic pain, chronic pain or brain cancer.

14. The method of claim 12, wherein the disease or condition is HIV.

15. A method of preventing or decreasing opioid-induced susceptibility to HIV infection in a subject in need thereof, comprising
administering to the subject a therapeutically effective amount of at least one bivalent ligand of claim 1.

16. The method of claim 15, wherein the therapeutically effective amount is sufficient to permit the at least one bivalent ligand to bind to MOR-CCR5 heterodimers on cells of the subject.

17. A method of preventing or decreasing opioid-accel-erated HIV-1 entry into a cell, comprising
contacting the cell with at least one bivalent ligand of claim 1, wherein the step of contacting is performed under conditions that permit the bivalent ligand to bind to and form a complex with MOR-CCR5 heterodimers on the cell, and wherein formation of the complex prevents or decreases opioid-accelerated HIV entry into the cell.

* * * * *